US010463699B2

(12) United States Patent
Bettle, III

(10) Patent No.: US 10,463,699 B2
(45) Date of Patent: Nov. 5, 2019

(54) FISH OIL TOPICAL COMPOSITION

(71) Applicant: Omeza LLC, Longboat Key, FL (US)

(72) Inventor: Griscom Bettle, III, Sarasota, FL (US)

(73) Assignee: Omeza LLC, Longboat Key, FL (US)

( * ) Notice: Subject to any disclaimer, the term of this patent is extended or adjusted under 35 U.S.C. 154(b) by 17 days.

(21) Appl. No.: 15/478,889

(22) Filed: Apr. 4, 2017

(65) Prior Publication Data

US 2017/0281689 A1 Oct. 5, 2017

Related U.S. Application Data

(60) Provisional application No. 62/390,631, filed on Apr. 4, 2016.

(51) Int. Cl.

| | |
|---|---|
| ***A61K 35/60*** | (2006.01) |
| ***A61K 9/00*** | (2006.01) |
| ***A61K 36/889*** | (2006.01) |
| ***A61K 38/39*** | (2006.01) |
| ***A61K 47/14*** | (2017.01) |
| ***A61K 9/06*** | (2006.01) |
| ***A61K 31/202*** | (2006.01) |

(52) U.S. Cl.
CPC ............ *A61K 35/60* (2013.01); *A61K 9/0014* (2013.01); *A61K 9/06* (2013.01); *A61K 31/202* (2013.01); *A61K 36/889* (2013.01); *A61K 38/39* (2013.01); *A61K 47/14* (2013.01)

(58) Field of Classification Search
None
See application file for complete search history.

(56) References Cited

U.S. PATENT DOCUMENTS 3,152,181 A 10/1964 Shapiro et al.
5,164,193 A 11/1992 Okada et al.
5,545,402 A 8/1996 Watkinson
5,665,366 A 9/1997 Rawlings et al.
5,773,457 A 1/1998 Nahoum
5,725,880 A 3/1998 Hirakawa et al.
5,908,853 A 6/1999 Nahoum
5,952,361 A 9/1999 Dias Nahoum
6,468,551 B1 10/2002 Diec et al.
6,607,733 B1 8/2003 Diec et al.
6,613,338 B1 9/2003 Schreiber et al.
6,638,981 B2 10/2003 Williams et al.
6,758,099 B2 7/2004 Cima et al.
6,846,796 B2 1/2005 Schmid
6,852,526 B2 2/2005 Cima et al.
6,919,076 B1 7/2005 Green et al.
6,958,148 B1 10/2005 Green et al.
7,172,859 B2 2/2007 Cima et al.
7,297,668 B2 11/2007 Johansson et al.
7,811,594 B2 10/2010 Schreiber et al.
7,972,630 B2 7/2011 Lidgren
7,994,138 B2 8/2011 Awada et al.
8,153,561 B2 4/2012 Messerschmidt et al.
8,318,678 B2 11/2012 Marini
8,329,200 B2 12/2012 Bauer et al.
8,394,759 B2 3/2013 Barathur et al.
8,465,552 B2 6/2013 Martinez-Santiago et al.
8,592,401 B2 11/2013 Petkovich et al.
8,603,440 B2 12/2013 Andersen et al.
8,623,331 B2 1/2014 Andersen et al.
8,680,060 B2 3/2014 Awada et al.
8,722,022 B2 5/2014 Andersen et al.
8,802,087 B2 8/2014 Shlieout et al.
8,815,257 B2 8/2014 Braksmayer et al.
8,865,695 B2 10/2014 Giliyar et al.
8,951,996 B2 2/2015 Giliyar et al.
8,968,770 B2 3/2015 Pedersen et al.
8,975,237 B2 3/2015 Becker et al.
9,023,878 B2 5/2015 Baker
9,040,591 B2 5/2015 Devane
9,062,131 B2 6/2015 Lepilleur et al.
9,078,827 B2 7/2015 Odidi et al.
9,180,084 B2 11/2015 Lepilleur et al.
9,358,299 B2 1/2016 Giliyar et al.
9,283,191 B2 3/2016 Andersen et al.
9,358,298 B2 6/2016 Giliyar et al.
9,364,547 B2 6/2016 Giliyar et al.
9,371,489 B2 6/2016 Rehage
9,388,343 B2 7/2016 Rehage
9,399,069 B2 7/2016 Giliyar et al.
9,446,226 B2 9/2016 Zilberman
9,499,419 B2 11/2016 de Rijk
9,522,119 B2 12/2016 Odidi
9,526,692 B2 12/2016 Rehage
(Continued)

FOREIGN PATENT DOCUMENTS

WO 2010/036578 A1 4/2010
WO 2016/089200 A1 6/2016

OTHER PUBLICATIONS

Yi, J., et al., Food Chemistry 127: 1792-1797 (2011) . (Year: 2011).*
(Continued)

*Primary Examiner* — David J Blanchard
*Assistant Examiner* — Daniel F. Coughlin
(74) *Attorney, Agent, or Firm* — Scully Scott Murphy and Presser

(57) ABSTRACT

Disclosed is a method of reducing the rancid fish odor smell in a topical composition comprised of fish oil which comprises mixing the composition with monolaurin. Also disclosed are various anhydrous topical compositions comprising fish oil. One comprises fish oil, cetyl ester, palm olein, medium-chain triglyceride(s) of a mixture of C8 and C10 fatty acids, mixture of C8/C10 fatty acids, and monolaurin, another one comprises fish oil, cetyl ester, palm olein, medium-chain triglyceride(s) of a mixture of C8 and C10 fatty acids, mixture of C8/C10 fatty acids, monolaurin, collagen and sea salt, an a third one comprises fish oil, cetyl ester, palm olein, medium-chain triglyceride(s) of a mixture of C8 and C10 fatty acids, mixture of C8/C10 fatty acids, monolaurin and hydrocolloid. These compositions are useful for treating wounds and skin conditions.

50 Claims, No Drawings

(56) References Cited

U.S. PATENT DOCUMENTS 9,561,188 B2 2/2017 Odidi et al.
2002/0025509 A1 2/2002 Cima et al.
2002/0146375 A1 10/2002 Schreiber et al.
2002/0155084 A1 10/2002 Roessler et al.
2003/0068614 A1 4/2003 Cima et al.
2003/0082214 A1 5/2003 Williams et al.
2003/0130155 A1 7/2003 Schmid
2003/0161858 A1 8/2003 Lidgren
2003/0170610 A1 9/2003 Cima et al.
2003/0180352 A1 9/2003 Patel et al.
2004/0076648 A1 4/2004 Williams et al.
2004/0087007 A1 5/2004 Cima et al.
2004/0209961 A1 10/2004 Devane
2004/0235145 A1 11/2004 Cima et al.
2004/0258721 A1 12/2004 Bauer et al.
2004/0260318 A1 12/2004 Hunter et al.
2005/0106199 A1 5/2005 Schreiber et al.
2005/0124705 A1 6/2005 Schreiber et al.
2005/0142153 A1 6/2005 Schreiber et al.
2005/0249763 A1 11/2005 Legendre et al.
2005/0250817 A1 11/2005 Shlieout et al.
2005/0266036 A1 12/2005 Awada et al.
2006/0002964 A9 1/2006 Schreiber et al.
2006/0008537 A1 1/2006 Wu et al.
2006/0009499 A1 1/2006 Wu et al.
2006/0024361 A1 2/2006 Odidi et al.
2006/0093571 A1 5/2006 Glinski
2006/0104966 A1 5/2006 Green et al.
2006/0110379 A1 5/2006 Green et al.
2007/0049496 A1 3/2007 Messerschmidt et al.
2007/0134305 A1 6/2007 Zilberman
2007/0154575 A1* 7/2007 Shimoda ............ A61K 31/7008 424/756
2007/0224284 A1 9/2007 Devane
2007/0248633 A1 10/2007 Baldo
2008/0008673 A1 1/2008 Willemin et al.
2008/0182293 A1 7/2008 Lemmo et al.
2008/0199420 A1 8/2008 Wendel et al.
2008/0207766 A1 8/2008 Devane
2009/0214628 A1 8/2009 de Rijk
2009/0220443 A1 9/2009 Braksmayer et al.
2009/0220613 A1 9/2009 Odidi et al.
2009/0232887 A1 9/2009 Odidi et al.
2009/0324663 A1 12/2009 Legendre et al.
2010/0029574 A1 2/2010 Marini
2010/0173882 A1 7/2010 Giliyar et al.
2010/0196479 A1 8/2010 Devane
2010/0204189 A1 8/2010 Petkovich et al.
2010/0255063 A1 10/2010 Andersen et al.
2010/0255064 A1 10/2010 Andersen et al.
2010/0266666 A1 10/2010 Andersen et al.
2011/0064783 A1 3/2011 Bang-Madsen et al.
2011/0065627 A1 3/2011 Barathur et al.
2011/0092449 A1 4/2011 Duft
2011/0136890 A1 6/2011 Becker et al.
2011/0142897 A1 6/2011 Cotton et al.
2011/0250150 A1 10/2011 Pedersen et al.
2012/0058895 A1 3/2012 Awada et al.
2012/0225106 A1 9/2012 Ross et al.
2012/0317734 A1 12/2012 Martinez/Santiago et al.
2013/0017239 A1 1/2013 Viladot Petit et al.
2013/0029957 A1 1/2013 Giliyar et al.
2013/0030057 A1 1/2013 Devane
2013/0034505 A1 2/2013 Lepilleur et al.
2013/0058983 A1 3/2013 Baker
2013/0071535 A1 3/2013 Fenyvesi et al.
2013/0085067 A1 4/2013 Schofield et al.
2013/0129639 A1 5/2013 Anderson et al.
2013/0142855 A1 6/2013 Gross et al.
2013/0156708 A1 6/2013 Pesaro et al.
2013/0177504 A1 7/2013 Macoviak
2013/0189211 A1 7/2013 Marini
2013/0209585 A1 8/2013 Kim
2013/0216596 A1 8/2013 Viladot Petit et al.
2013/0331466 A1 12/2013 Gross et al.
2014/0010860 A1 1/2014 Odidi et al.
2014/0066415 A1 3/2014 Petkovich et al.
2014/0079756 A1 3/2014 Andersen et al.
2014/0127149 A1 5/2014 Lepilleur et al.
2014/0178466 A1 6/2014 Giliyar et al.
2014/0178496 A1 6/2014 Macoviak et al.
2014/0179652 A1 6/2014 Giliyar et al.
2014/0205546 A1 7/2014 Macoviak
2014/0260466 A1 9/2014 Rehage
2014/0271882 A1 9/2014 Giliyar et al.
2014/0271928 A1 9/2014 Rehage
2014/0302000 A1 10/2014 Shlieout et al.
2014/0357714 A1 12/2014 Braksmayer et al.
2014/0377317 A1 12/2014 Giliyar et al.
2015/0099681 A1 4/2015 Rehage
2015/0165049 A1 6/2015 Giliyar et al.
2015/0190406 A1 7/2015 Giliyar et al.
2015/0216985 A1 8/2015 Macoviak et al.
2015/0232842 A1 8/2015 Becker et al.
2015/0250733 A1 9/2015 Odidi
2015/0297734 A1 10/2015 Odidi et al.
2015/0320768 A1 11/2015 Giliyar et al.
2015/0335686 A1 11/2015 Spencer et al.
2016/0008410 A1 1/2016 Spencer et al.
2016/0015031 A1 1/2016 Pesaro et al.
2016/0022590 A1 1/2016 Odidi
2016/0058772 A1 3/2016 Baker
2016/0100574 A1 4/2016 Pesaro et al.
2016/0213686 A1 7/2016 Giliyar et al.
2016/0298037 A1 10/2016 Rehage
2016/0310375 A1 10/2016 Torres Rivera et al.
2016/0310376 A1 10/2016 Torres Rivera et al.
2016/0310377 A1 10/2016 Torres Rivera et al.
2016/0346294 A1* 12/2016 Sengupta ............... A61K 45/06
2016/0346332 A1 12/2016 Spencer et al.
2016/0375034 A1 12/2016 Baker et al.
2017/0007623 A1 1/2017 Giliyar et al.
2017/0027962 A1 2/2017 Petkovich et al.
2017/0035781 A1 2/2017 Giliyar et al.
2017/0065519 A1 3/2017 Zilberman
2017/0071214 A1 3/2017 Rehage

OTHER PUBLICATIONS

Itnernational Search Report dated Aug. 14, 2017 & Written Opinion dated Jul. 4, 2017 issued in International Application No. PCT/US2017/025941.

* cited by examiner

FISH OIL TOPICAL COMPOSITION

CROSS-REFERENCE TO RELATED APPLICATION

The present application is claiming benefit of U.S. Ser. No. 62/390,631, which was filed on Apr. 4, 2016, the contents of which are incorporated by reference.

FIELD OF THE DISCLOSURE

The present disclosure relates to a topical composition comprised of fish oil containing omega-3 fatty acids for treating wounds and skin disorders.

BACKGROUND OF THE DISCLOSURE

Fish oil contains, among other components, omega 3-fatty acids. Omega-3 (n-3) fatty acids have a variety of anti-inflammatory and immune-modulating effects that may be of relevance to diseases and conditions where inflammation is an underlying cause. Inflammation is the body's attempt at self-protection where the aim is to remove harmful stimuli and start the healing process. Inflammation may be divided into acute and chronic inflammation where the acute inflammation starts rapidly and quickly becomes severe. Examples of acute inflammation may e.g. be acute bronchitis or acute appendicitis. Chronic inflammation may e.g. be failure to eliminate the causing agent, an autoimmune response to a self antigen or a chronic irritant of low intensity that persists. Chronic inflammation may however, mature into severe diseases such as chronic obstructive pulmonary disease (COPD), cancer, atherosclerosis, Alzheimer's disease (AD), amyotrophic lateral sclerosis (ALS) etc.

The omega-3 fatty acids are essential to life at any stage, even before birth. They are essential building blocks of the membrane of every cell in the body and their presence are a necessity for maintaining an adequate cell membrane. They do also contribute in the regulation of most biological functions.

The richest dietary source of long-chain omega-3 polyunsaturated fatty acids (PUFA) comes from fish oil. Fatty acids are the building blocks of dietary fats, and are stored substantially in the form of triglycerides. The body cannot however, produce these fatty acids and must obtain them from food sources or from supplements. Three fatty acids compose the omega-3 family: alpha-linolenic acid (ALA), eicosapentaenoic acid (EPA) and docosahexaenoic acid (DHA). ALA is found in e.g. walnuts, some types of beans and olive oils. EPA and DHA are found in fish, including fish oil and supplements.

Resolvins and protectins are oxygenated metabolites derived from EPA and DHA, and a part of the molecular mechanisms contributing to removal of inflammatory cells and restoration of tissue once the need for inflammatory response is over. It has been shown that aspirin treatment enhances the conversion of EPA and DHA to resolvins which carry potent anti-inflammatory signals. The mechanisms by which their effects are exerted are still a matter of controversy, but it seems likely that said oxygenated metabolites play a significant role as they have potent anti-inflammatory and immunoregulatory actions even in concentrations in the nanomolar and picomolar range. As tissues return to normal, resolvins and protectins together with further oxygenated metabolites as lipoids and mare sins promote resolution of the inflammation through removal of leucocytes and cellular debris.

A recent study at Brigham and Women's Hospital in Boston revealed that omega-3s actually convert into compounds that are 10,000 times more potent than the original fatty acids themselves. These compounds include resolvins, which help bring an inflammatory response in the body to an end.

However, one of the problems associated with the use of fish oil is the strong fishy odor associated therewith that lingers and lingers. Because of the long-lasting fish odor, many topical compositions do not contain fish oil as an active ingredient. Moreover, even if fish oil is contained in topical compositions, consumers are reluctant to use those compositions because of the long-lasting odor. However, the present inventor has found a way to eliminate the fishy smell.

SUMMARY

The present disclosure is directed to, in an embodiment, a method for removing the rancid fish smell from a topical collagen composition comprising fish oil and collagen comprising mixing the fish oil with monolaurin in a weight ratio of fish oil to monolaurin ranging from about 100:1 to about 25:1. An embodiment thereof is additionally adding cetyl esters thereto. Another aspect of the present disclosure is directed to an improved topical fish oil composition comprising fish oil but in the absence of collagen, the improvement comprising the composition additionally comprising monolaurin, the weight ratio of fish oil to monolaurin (without collagen) ranging from about 160:1 to about 50:1. Another aspect of the present disclosure is adding cetyl esters thereto. A further aspect of the present disclosure is directed to a topical composition comprising fish oil; palm olein; C8 fatty acid, C10 fatty acid or mixture thereof, wherein if there is a mixture, the free fatty acids of C8 to C10 is present in a weight ratio of C8 to C10 fatty acid of 1.3 to 1.6; medium-chain triglyceride(s) of a C8 fatty acid, or triglyceride of a C10 fatty acid or a mixture of C8 and C10 fatty acids comprising 51% by weight of a triglyceride of C8 fatty acid and about 49% by weight of a triglyceride of C10 fatty acid: cetyl ester and monolaurin ("emollient composition"). In an embodiment, there is a greater amount of cetyl ester present than monolaurin, for example, the weight ratio of cetyl ester to monolaurin per gram of fish oil ranges from about 1.1 to about 3:1. Another aspect of the present invention is directed to a topical composition comprising fish oil; palm olein; C8 fatty acid, C10 fatty acid, or a mixture of free fatty acids of C8 to C10 in a weight ratio of C8 to C10 fatty acid of 1.3 to 1.6; triglyceride(s) of a C8 fatty acid, triglyceride of a C10 fatty acid, or a mixture of a medium chain triglyceride of a mixture of C8 and C10 fatty acids comprising 51% by weight of a triglyceride of C8 fatty acid and about 49% by weight of a triglyceride of C10 fatty acid, cetyl ester, monolaurin, collagen and sea salt ("collagen composition"). In an embodiment, in the collagen composition, there is a greater amount of monolaurin present than cetyl ester, for example, in some embodiments of the collagen composition, there is no cetyl ester present, while in other embodiments of the collagen composition, the weight ratio of monolaurin to cetyl ester per gram of fish oil ranges from about 3:1 to about 9:1. In another aspect in both the emollient and collagen compositions, the fish oil is salmon oil. In another aspect in both the emollient and collagen compositions, the amount of fish oil is present in significantly greater amounts by weight than cetyl ester, for example, the weight ratio of fish oil to cetyl ester ranges from about 40:1 to about 60:1. In a farther aspect of the present disclosure, in both the collagen and emollient compositions, the weight ratio of C8/C10 fatty acid to cetyl ester is about 2:1. In another aspect of the present disclosure, the amount of fish oil is present in significantly greater amounts by weight than palm olein, for example the weight ratio of fish oil to palm olein ranges from about 6:1 to about 1.5:1. In a further aspect of the present disclosure, in both the emollient and collagen compositions, the weight ratio of medium-chain triglyceride(s) of C8/C10 fatty acids and C8/C10 fatty acids ranges from about 10:1 to about 25:1. Further, in another aspect of the present disclosure, the fish oil is present in greater amounts by weight than the medium-chain triglyceride(s) of C8/C10 fatty acids, for example, the weight ratio of fish oil to of C8/C10 fatty acids ranges from about 1.1:1 to about 3:1. In addition, in a further aspect of the present disclosure, in both the emollient and collagen compositions, the amount of medium-chain triglyceride(s) of C8/C10 fatty acids is present in greater amounts by weight than the palm olein. For example, the weight ratio of medium-chain triglyceride(s) of C8/C10 fatty acids to palm olein is about 1.3:1 to about 4:1. Another aspect of the present disclosure is directed to an anhydrous topical composition comprising fish oil in an amount ranging from about 40% to about 60% by weight, palm olein present in an amount ranging from about 10% to about 20% by weight, C8/C10 free fatty acid present in an amount ranging from about 0.5% to about 4% by weight, medium-chain triglyceride(s) of C8/C10 fatty acids present in an amount ranging from about 25% to 35% by weight, cetyl ester ranging from about 1.0% to about 2% by weight and monolaurin, ranging from about 0.5% to about 2% by weight, wherein the weight ratio of the sum of the saturated compounds in the salmon oil, palm olein and triglyceride of C8/C10 fatty acids to the sum of the mono-unsaturated compounds in the salmon oil, palm olein and triglyceride of C8/C10 fatty acids ranges from about 1.8 to about 2.2, wherein the sum of the dry weight percent of all of the components present is equal to 100%. Another aspect of the present disclosure is directed to a composition comprising fish oil present in an amount ranging from about 20% to about 40% by weight, palm olein present in an amount ranging from about 6% to about 10% by weight, C8/C10 free fatty acid present in an amount ranging from about 0.3% to about 3% by weight; a medium-chain triglyceride(s) of C8/C10 fatty acids present in an amount ranging from about 14% to 18% by weight, cetyl ester ranging from about 0.3% to about 1% by weight; monolaurin ranging in an amount ranging from about 3% % to about 6% by weight; collagen having a glass transition temperature of less than 37° C. ranging in an amount ranging from about 35% to about 55% by weight and sea salt ranging in an amount from about 0.3 to about 0.9% by weight wherein the weight ratio of the sum of the saturated compounds in the salmon oil, palm olein and triglyceride mixture of C8 and C10 fatty acids to the sum of the mono-unsaturated compounds in the salmon oil, palm olein and triglyceride mixture of C8 and C10 fatty acids ranges from about 1.8 to about 2.2, wherein the sum of the dry weight % of all of the components present in the composition being 100%. Both the emollient formulations and the collagen formulations oil fraction are single phase oils in the temperature range of −5° C. to about 35° C. Another aspect of the present disclosure is directed to a topical emollient composition comprising a combination of one or more of the embodiments described hereinabove applicable to it. A further aspect is directed to a topical collagen composition comprising a combination of one or more of the aforesaid embodiments described hereinabove applicable to it.

In addition, an aspect of the present disclosure is directed to treating a skin disorder or wound on a subject by topically applying an effective amount of the emollient composition or collagen composition or combination thereof to the area where the skin disorder or wound is located. A further aspect of the present disclosure is directed to treating a skin disorder or wound on a subject by first topically applying an effective amount of the emollient composition, then topically applying an effective amount of the collagen composition to the area where the skin disorder or wound is located.

DETAILED DESCRIPTION

As described hereinabove, the useful component obtained from fish oil for example, is the omega-3 fatty acids. The omega-3 fatty acids can be isolated from various marine life. For example, they are found in fish oil. As defined herein, "fish oil" refers to the oil extracted from fish carcasses or crustaceans or any other marine life. Examples of fish where the useful oil containing omega-3 fatty acids include is salmon, tuna, swordfish, halibut, tilefish, cod fish (including cod fish oil), anchovies and sardines. Cold-pressed fish oil and heat treated fish oil are subsumed under the term "fish oil". Examples of crustaceans from which the oil can be used include krill, a crustacean in the Antarctic (the source of krill oil) and the New Zealand green lipped mussel (also known as *Perna canaliculus*). In addition, useful oil is derived from marine vegetation, such as Marine algae and phytoplankton can also be used. All of these oils are a source of omega-3 fatty acids. The term fish oil, as used herein, refers to the marine sources containing omega 3-fatty acids. Nutritionally important omega-3 fatty acids include α-linolenic acid (ALA) (18 carbon unsaturated fatty acid), Eicosapentaenoic acid (EPA) (20 carbon insaturated fat) and docosahexaenoic acid (DHA) (22 carbon unsaturated fatty acid).

Omega-3 fatty acids can be derived from a vegetable source, such seed oils. Including *perilla* seeds (Linnaean name *Perilla frutescens*); chia seeds (*Salvia hispanica*); flax seeds (*Linum usitatissimum*); lingon berry seeds (*Vaccinium vitis-idaea*); and rape seeds (*Brassica napus*), more commonly called canola oil. However, as defined herein, the omega 3-oils derived from vegetable sources are excluded from the definition of fish oil. Thus, the omega-3 fatty acids used in the present compositions described hereinbelow are derived from marine sources. In an embodiment, the fish oil used herein is derived from fish carcasses. In an embodiment, the fish oil utilized is salmon oil. Salmon oil also contains astaxanthin, which is a powerful anti-oxidant.

As defined herein, the terms "mixture of C8/C10 fatty acids", "C8/C10 fatty acid" and "C8/C10 fatty acids", which are interchangeable, refer to a free C8 fatty acid or free C10 fatty acid or a mixture thereof. As used herein, the fatty acids are caprylic acid (C8 fatty acid), capric acid (C10 fatty acid) or a mixture thereof. In an embodiment, the free fatty acids are a mixture of caprylic and capric acid. In an embodiment, the amount of C8 fatty acid present by weight is greater than the amount of C10 fatty acid present by weight. For example, in an embodiment, the weight ratio of C8 fatty acid to C10 fatty acid ranges from about 1.8 to about 1.1, while in another embodiment it ranges from about 1.6 to about 1.3. Capric/caprylic fatty acid is typically a natural product derived from coconut oil. Commercial product ranges from about 53% to about 63% C8 and about 47% to about 37% by weight C10. Thus, in an embodiment, the weight ratio of C8 fatty acid to C10 fatty acid ranges from about 53:47 to about 63:37, which is a ratio range of about 1.13 to about 1.71.

The term "medium-chain triglyceride(s) of C8/C10 fatty acid", "medium-chain triglyceride(s) of C8/C10 fatty acids", "medium-chain triglycerides of a mixture of C8 and C10 fatty acids" and "C8/C10 triglycerides", are interchangeable and refer to a triglyceride of C8 fatty acid, a triglyceride of C10 fatty acid or a mixture thereof. In addition, the term C8 triglyceride refers to a triglyceride of a C8 fatty acid, and the term C10 triglyceride refers to a triglyceride of a C10 fatty acid. In an embodiment, it is a mixture of triglycerides of C8 and C10 fatty acids, wherein the amount by weight of triglycerides of C8 fatty acids present is greater than the amount by weight of triglycerides C10 present. In an embodiment, it comprises a mixture of about 51% C8 triglycerides and about 49% C10 triglycerides to about 70% C8 triglycerides to about 30% C10 triglycerides by weight; in another embodiment, it comprises 55% C8 triglycerides and about 45% C10 triglycerides to about 65% C8 triglycerides to about 35% C10 triglycerides by weight and in a further embodiment, it comprises an average weight ratio of C8 triglycerides to C10 triglycerides of about 60/40. The three chain fatty acids that are attached to the triglyceride backbone of may be, but need not be, identical, and the fatty acids can be either saturated or unsaturated, but are preferably saturated. The term includes medium chain triglycerides (MCT). An MCT comprises a triglyceride backbone having attached thereto three fatty acid chains that are generally from about C6 to C12 in length, although shorter or longer chains may be included within the term in differing contexts, as understood by those having skill in the art. The three medium chain fatty acids that are attached to the triglyceride backbone of the MCT may be, but need not be, identical. The medium chain fatty acids can be either saturated or unsaturated, but are preferably saturated. Examples of medium chain fatty acids that comprise the medium chain triglycerides of the invention include C6 (caproic fatty acid), C8 (caprylic fatty acid), C10 (capric fatty acid), and C12 (lauric fatty acid), as well as mixtures thereof. In an embodiment, the MCTs comprise a mixture of from about 60% C8 triglyceride and about 40% C10 triglyceride to a mixture of about 70% C8 triglyceride and about 30% triglyceride C10. Further, the MCTs of the present invention may include minor amounts of triglycerides of short or long chain fatty acids, such as C6 or C4 fatty acids or C14 or C16 fatty acids, but the short or long fatty acids are present in minor amounts, e.g., less than 3% by weight. In another embodiment, the MCT contains no triglyceride of a C12 fatty acid.

The medium-chain triglyceride(s) of C8/C10 fatty acids are prepared by chemical techniques known in the art by esterifying the fatty acid to glycerol.

As used herein, palm olein is the liquid portion which is separated from the semi-solid palm oil by fractionation. As used herein, the term includes red palm olein, and super red palm olein. The liquid portion is sold as cooking oils and the solid portion is known as "palm stearin". When palm olein is fractionated again to get a more liquid fraction, such as by chilling and removing the solid fraction of C18:0 (saturated C18 fatty acids). It is known as "super palm olein". Palm super olein is capable of withstanding colder temperature in comparison with palm olein after which they turn into solid. Palm olein is commonly used as cooking oil in the tropical countries. But the problem in temperate countries is that due to cold weather it tends to get cloudy and crystallize. To overcome this problem, palm olein is blended with more unsaturated vegetable oils. This blended form can be used in a wide range of climates and has a better cold stability. These blends are also cheaper than non-blended forms. The vegetable oils from rice bran, groundnuts and rapeseed are blended with palm olein to get a superior form in terms of quality and stability.

Red palm oil is obtained from the endocarp of the palm fruit (the soft flesh); palm oil is obtained from the seed (palm kernel oil). The oils are very much different. Red palm oil has the highest level of antioxidants of any seed crop. The carotenoids and tocotrienols present therein give red palm oil its distinctive color. These highly colored compounds are not readily absorbed by the skin and stain the skin surface and any clothing or bedding surface it comes in contact with.

In an embodiment, the palm oil, the red palm olein, and the super red palm olein contains a low amount of saturated C18 fatty acid. By low amount, it means less than 0.5% by weight.

Monolaurin, as used herein, is also known as glycerol monolaurate, glyceryl laurate or 1-Lauroyl-glycerol. It is a monoglyceride. It is the mono-ester formed from glycerol and lauric acid. Its chemical formula is $C_{15}H_{30}O_4$.

Cetyl ester, as defined herein, is an ester formed from cetyl alcohol and a C14, C16 or C18 fatty acid. The fatty acids may be saturated or unsaturated. As used herein, cetyl ester refers to C14, C16, or C18 fatty acid or mixtures thereof. In an embodiment, cetyl ester is Cetyl Ester NF, CAS 977067-67-6.

Sea salt, as used herein, is the salt produced from the evaporation of seawater. The sea salt used herein may be refined or unrefined. The colors and variety of flavors in sea salt are due to local days and algae found in the waters the salt is harvested from. For example, some boutique salts from Korea and France are pinkish gray, some from India are black. The chemical composition of sea salt is typically the same as the ions dissolved in seawater. By dry weight percent: Sodium, 30.8; Potassium, 1.1; Magnesium, 3.7; Calcium, 1.2; Chloride, 55.5; Sulfate, 7.7. Thus, the sea salt used herein contains, as a minimum, those aforesaid ions. However, a study found the amount of trace elements, such as titanium, silver, cobalt, and lead in synthetic sea salt are much higher than those in sea water. The magnitude of the difference can be as large as $10^4$ times. Unrefined sea salt contains small amounts of magnesium and calcium halides and sulphates, traces of algal products, salt-resistant bacteria and sediment particles. The calcium and magnesium salts confer a faintly bitter overtone, and they make unrefined sea salt hygroscopic (i.e., it gradually absorbs moisture from air if stored uncovered). Algal products contribute a mild "sea-air" smell, the latter from organobromine compounds. Sediments, the proportion of which varies with the source, give the salt a dull grey appearance.

Collagen is a main protein component constituting connective tissue in animals and is characterized by having a collagen triple helical structure. A total of not less than 30 types of collagens have been reported which are respectively termed Type I, Type II, and so on. Type I collagen is the primary component of the derma, ligaments, tendons, bones and the like; and Type II collagen is the primary component of articular cartilage. Further, Type IV collagen is mainly contained in a basal membrane, which is the undercoat of all epithelial tissues. Type I collagen is the most abundant collagen in the body.

In the present invention, the collagen origin is not limited, and usable are those derived from mammals such as cow, pig, etc., birds such as chicken, ostrich, etc., fishes such as sharks, etc. Those derived from livestock such as cow, pig, chicken, etc., are easily obtainable in a large amount. Further, the type of collagen is not limited and any type can be used, or a plurality of collagen types may be used in mixture.

In the present invention, the collagen used is a collagen hydrolysate (hereinafter sometimes referred to as collagen peptide) and it refers to a low molecular weight collagen obtained by hydrolyzing collagen with an acid, alkali or enzyme. For example, a collagen hydrolysate can be obtained by immersing skins and joints of animals such as pig, cow and chicken or scales and skins of fish in an acid or alkali solution to extract gelatin and treating the extracted gelatin with an enzyme or acid. The gelatin refers to the collagen pre-treated with an acid or alkali and then solubilized by heat hydrolysis. In an embodiment, the collagen is derived from marine life, such as cold-water fish. Cold water fish come from unpolluted water and do not have diseases associated with land animals.

The collagen used in the present invention has a $T_g$ (glass transition temperature)<37° C. (normal body temperature). Practically this means that any marine collagen from a cold-water source is acceptable. An example is fish collagen. On the other hand, bovine, hog, horse collagen are not useful and are not included in the definition of collagen used herein.

The term "oils", when used alone, refers to the combination of fish oil, C8/C10 triglyceride and palm olein.

Treatment" or "treating," as used herein refers to complete elimination as well as to any clinically or quantitatively measurable healing or alleviation of the symptoms of the wound.

A "therapeutically effective amount" means the amount of a composition that, when administered to a subject for treating a wound, is sufficient to effect a desirable treatment for the wound. The "therapeutically effective amount" will vary depending on the particular composition, the condition and its type and severity, and the age, weight, etc., of the subject to be treated. The actual amount which comprises the "effective amount" will vary depending on a number of conditions including, but not limited to, the particular disorder being treated, the severity of the disorder, the size and health of the patient, and the route of administration. A skilled medical practitioner can readily determine the appropriate amount using methods known in the medical arts.

"Patient" or "subject" refers to animals, and can include any mammal, such as humans, rats, mice, cats, dogs, goats, sheep, horses, monkeys, apes, rabbits, cattle, etc. The mammalian subject can be in any stage of development including adults, children, infants, and neonates.

Unless indicated to the contrary, percentages are by weight and ratios are weight ratios.

As used herein, the singular forms "a", "an" and "the" include plural referents unless the context clearly dictates otherwise.

An embodiment of the present invention is the reduction or elimination of the rancid fish smell associated with fish oil when used in a topical composition which additionally does not contain collagen. The present inventor has found that the addition of monolaurin to the fish oil composition reduces or eliminated completely the rancid fish odor. An aspect of the present invention is to eliminate or reduce the smell of fish oil by mixing it with monolaurin in a weight ratio of fish oil to monolaurin ranging from about 200 to about 70. If the level of monolaurin is low, the desired odor effect is trivial. If the level of monolaurin is high, a syrupy gel forms that makes a two-phase sticky fluid. In an aspect, the weight ratio ranges from about 60 to about 90 and in another embodiment; it ranges from about 75 to about 85. However, there is a maximum amount of monolaurin that can be present in the pharmaceutical composition; the monolaurin may not exceed 2% by weight of the oil composition comprised of fish oil. Above this amount, the monolaurin forms an unstable gel. In an embodiment, the monolaurin does not exceed 2% by weight, and in another embodiment, it does not exceed 1% by weight of the composition. However, the monolaurin should be present in the composition in an amount greater than 0.5 wt %.

In an embodiment, the fish oil is present in the topical composition at an amount ranging from about 30% to about 70% by weight, while in another embodiment, it is present in an amount ranging from about 35% to about 60% by weight, and in another embodiment, it is present in an amount ranging from about 40% to about 50% by weight of the composition When the monolaurin is mixed with fish oil and collagen, the weight ratios change. In an embodiment, the weight ratio of fish oil to monolaurin ranges from about 60:1 to about 90:1, and in another embodiment, from about 75:1 to about 85:1 and in another about 80:1. However, in an embodiment, wherein the fish oil is present in large amounts, such as greater than 10% by weight of the composition, or in another embodiment, over 15% by weight of the composition or in another embodiment, over 20% by weight of the composition, the monolaurin should also be present in at least 3.5% by weight of the composition.

When the monolaurin is mixed with the fish collagen, the undesirable gelling in the neat oil becomes a benefit in helping to bind oil to the collagen in an anhydrous base.

In addition, the present inventor has also found that another ingredient that helps remove the fishy odor is cetyl esters. In an embodiment, the cetyl ester is present in an amount ranging from about 0.5% to 2% by weight. In another embodiment, the cetyl ester is present in an amount ranging from about 1% to about 2% by weight of the composition. In an embodiment, the topical composition comprises fish oil in an amount ranging from about 30% by weight to about 70% by weight, monolaurin is present in an amount ranging from about 0.5% to about 2% by weight, and cetyl ester present in an amount ranging from about 1% to about 2% by weight. In an oil embodiment, the amount of cetyl ester present by weight is greater than the amount of monolaurin by weight.

Although cetyl esters also reduces the fishy smell, when used in combination with monolaurin in a topical fish oil composition that does not contain collagen. In an embodiment not containing collagen, per gram of fish oil, the weight ratio of cetyl ester to monolaurin ranges from about 1% to about 2%; in another embodiment, from about 1.3% to about 1.8%; and in a further embodiment, from about 1.6% to about 1.7%. If the composition contains collagen, there is a greater amount of monolaurin present than cetyl ester. In embodiments of the collagen composition, the weight ratio of monolaurin to cetyl ester per gram of fish oil ranges from about 3:1 to about 9:1, and in another embodiment, the weight ratio ranges from about 5:1 to about 7:1 and in another embodiment, the weight ratio is about 6:1. Nevertheless, in both formulations, the combination is more effective in removing the fishy smell than monolaurin or cetyl ester alone. Further, adding cetyl ester to the formulation created a silky smooth skin surface (finish) that is very pleasant to the touch.

With respect to the formulations described hereinbelow, without wishing to be bound, it is believed that the monolaurin helps drive the Omega-3 fats into the stratum corneum, leaving a residual of potentially oxidizable fat on the skin surface. The Cetyl Ester wax provides a late-drying odor-occlusive layer over any potentially oxidizable fat and over the free fatty acid (FFA). The net result is no odor after about 30 seconds. However, in an embodiment, the maximum amount of cetyl ester added is about 1% by weight of the composition. If more is used, e.g. 2% by weight, then the consumer perceives a waxy film instead of a silky smooth finish.

Embodiments of the present disclosure include two types of formulations described hereinbelow. Each of these formulations are single phase oils in the temperature range of about −5° C. to about 35° C. Each of the formulations are comprised of fish oil, palm olein and medium-chain triglyceride(s) of a mixture of C8 and C10 fatty acids. It was determined that the stability is achieved, i.e., being a single phase oil in the aforesaid temperature range, when the weight ratio of the sum of the saturated compounds divided by the sum of the mono-unsaturated compounds ranges from about 1.8 to about 2.2. These weight ratio is determined using the following table:

| | salmon | olein | C8/10 |
|---|---|---|---|
| C6:0 | | | 0 |
| C8:0 | | 0.034 | 59.7 |
| C10:0 | | 0 | 40.1 |
| C12:0 | 0.88 | 0.173 | 0.1 |
| C14:0 | 4.67 | 0.961 | |
| C15:0 | 0.54 | | |
| C16:0 | 12.79 | 42.465 | |
| C17:0 | 0.53 | | |
| C18:0 | 3.32 | 0.395 | |
| C20:0 | 0.12 | | |
| C22:0 | | 0.059 | |
| C23:0 | | 0.022 | |
| C24:0 | 2.98 | 0.067 | |
| C14.1 | 0.05 | | |
| C16.1 | 5.21 | | |
| C17.1 | 0.43 | | |
| C18:1 | 18.02 | 44.616 | |
| C20:1 | 6.96 | | |
| C22:1 | 6.65 | | |
| C24:1 | 0.63 | | |
| C18:2 | 2.10 | 10.372 | |
| C20:2 | 0.51 | | |
| C18:3 | 1.63 | 0.257 | |
| C20:3 | 0.40 | | |
| C18:4 | 2.63 | | |
| C20:4 | 2.60 | | |
| C20:5 | 10.12 | | |
| C22:5 | 0.20 | | |
| C22.6 | 12.00 | | |

In the table above, the term "olein" refers to palm olein, and the term C8/C10 refers to the weight percent of C8 triglycerides and C10 triglycerides in the medium-chain triglyceride(s) of a mixture of C8 and C10 fatty acids. The values in the first column are the number of carbon atoms present followed by the number of double bonds present in each compound in the aforesaid three components, wherein the number of double bonds range from 0 to 6. Thus, for example, a compound indicated to be 16:0 contains 16 carbon atoms and no double bonds, while a compound indicated as C22:1 has 22 carbon atoms and 1 double bond. For purposes of the calculation, the only values that matter are the saturated compounds (no double bonds) and mono-unsaturated compounds (having only one double bond).

The table above lists the weight % of each of the component oils in the blend. The weight % of palm olein, C8/10 triglyceride and salmon oil in the composition are multiplied by weight fractions of the saturated compounds in the table and added together to determine a value, which is the numerator. The weight percent of palm olein, C8/10 triglyceride and salmon oil in the composition are multiplied by weight fractions of the monounsaturated compounds in the table and added together to determine a value, which is the denominator. The numerator is divided by the denominator to obtain a ratio, which value ranges from about 1.8 to 2.2. In another embodiment, this value ranges from about 1.9 to about 2.1 and in a further embodiment, it ranges from about 1.95 to about 2.05, whole in another embodiment, the ratio is about 2.

This ratio is maintained in the emollient composition and in the collagen matrix of the collagen composition. Separately, the free fatty acid, monolaurin and cetyl ester are adjusted to make each product, but the ratios of the palm olein, C8/10 triglyceride and salmon oil are retained in both products.

In an embodiment, the present invention is directed to a first topical pharmaceutical composition comprised of fish oil containing omega-3 fatty acid present in an amount ranging from about 40% to about 60% by weight, palm olein present in an amount ranging from about 10% to about 20% by weight, C8/C10 fatty acids present in an amount ranging from about 0.5% to about 4% by weight, C8/C10 triglyceride present in an amount ranging from about 25% to 35% by weight, cetyl ester ranging from about 1.0% to about 2% by weight and monolaurin, ranging from about 0.5% to about 2% by weight, wherein the weight ratio of the sum of the saturated compounds in the salmon oil, palm olein and C8/C10 triglyceride to the sum of the mono-unsaturated compounds in the salmon oil, palm olein and C8/C10 triglyceride ranges from about 1.8 to about 2.2, wherein the sum of the dry weight % of all of the components present in the composition is 100%. This first type of composition is identified herein as the emollient composition. In another embodiment, the composition comprises fish oil, containing omega-3 fatty acid present in an amount ranging from about 45% to about 52% by weight, palm olein present in an amount ranging from about 14% to about 18% by weight, C8/C10 fatty acid present in an amount ranging from about 1% to about 3% by weight, C8/C10 triglyceride (present in an amount ranging from about 28% to 34% by weight, cetyl ester ranging from about 1.0% to about 2% by weight and monolaurin, ranging from about 0.5% to about 1.5% by weight, wherein the weight ratio of the sum of the saturated compounds in the salmon oil, palm olein and C8/C10 triglyceride to the sum of the mono-unsaturated compounds in the salmon oil, palm olein and C8/C10 triglyceride ranges from about 1.8 to about 2.2, wherein the sum of the dry weight % of all of the components present in the composition is 100%. In an embodiment, the first formulation is anhydrous.

In this emollient composition, the monolaurin is not to exceed 3.5% by weight as an unstable gel is formed at higher concentrations. More monolaurin does not help beyond the recommended range. In an embodiment, the monolaurin may be present from about 0.5% to about 1% by weight and in another embodiment, it is present in about 0.6% by weight.

Moreover, in this embodiment, the cetyl ester is present in an amount ranging from about 1% to about 2% by weight. However, the maximum amount is 2% by weight. If more than 2% by weight is added, the subject or patient perceives a waxy film instead of a silky smooth finish. If the cetyl ester is less than 1%, the subject or patient perceives a sticky finish.

In an embodiment, the fish oil is salmon oil. In another embodiment, the palm olein is red palm olein or red palm super olein. In another embodiment, the composition comprises salmon oil, red palm olein or red palm super olein, cetyl esters, MCT containing an average weight ratio of C8 triglyceride/C10 triglyceride of about 60:40 and a C8/C10 fatty acid mixture and monlaurin in the amounts described herein. In another embodiment, the composition comprises about 48% salmon oil by weight, about 16% red palm super olein by weight, about 1.0% cetyl ester by weight, about 0.6% monolaurin by weight, a mixture of C8/C10 free fatty acids in the ratios described hereinabove in about 2% by weight, and a mixture of C8/C10 fat in the ratio amounts described herein in about 32% by weight.

Another formulation of this first topical composition is as follows:

Salmon oil is present in about 47.8% by weight, super red palm olein is present in about 16% by weight, medium-chain triglyceride(s) of a mixture of C8 and C10 fatty acids is present at about 31.9% by weight, mixture of C8 and C10 fatty acid present in about 4% by weight and monolaurin being present at about 0.30% by weight.

The first topical composition is prepared by art recognized techniques. For example, they are prepared by thoroughly mixing the components at about 40° C. until the cetyl ester and monolaurin have melted. The time at 40° C. should be minimal to prevent vitamin destruction. The headspace in the mixing vessel should be an inert gas, such as argon, helium, and nitrogen and the like. In an embodiment, argon is used. Argon has the advantage of being heavier than air and helps prevent oxygen ingress into the mixing vessel headspace. Once the melt is achieved, the composition is cooled rapidly to room temperature by placing in an ice bath or in a cold jacketed tank. The order of addition is not critical because the mixture is a single-phase fluid once the room temperature solids melt. A homogenous oil is formed. This first topical formulation does not exhibit a rancid fishy oil smell.

Without wishing to be bound, it is believed that monolaurin acts as a process aid as it affects gelation. The monolaurin helps fish oil be absorbed by unbroken skin. It is believed that the faster the fish oil is absorbed, the less oxidation odor is generated.

Moreover, there is a synergy of cetyl esters with monolaurin. Without wishing to be bound, it is believed that the monolaurin helps drive the Omega-3 fats into the stratum corneum, leaving a residual of potentially oxidized fat on the skin surface. The Cetyl Ester wax provides a late-drying odor-occlusive layer over any potentially oxidized fat and over the free fatty acid (FFA). The net result is no odor after about 30 seconds.

A second type of topical formulation comprises collagen in addition to the fish oil and monolaurin and cetyl alcohol (hereinafter called the collagen composition). Since collagen is one of the larger ingredients, the amount of each of the other ingredient also changes. In this second topical formulation, in an embodiment, the amount of fish oil present ranges from about 20% to about 40% by weight, palm olein is present in an amount ranging from about 6% to about 10% by weight, C8/C10 triglyceride is present in an amount ranging from about 14% to 18% by weight, cetyl ester is present in an amount ranging from about 0.3% to about 1% by weight; C8/C10 fatty acid is present in an amount ranging from about 0.3% to about 3% by weight; monolaurin is present in an amount ranging from about 3% to about 6% by weight; collagen having a glass transition temperature of about 37° C. ranging from about 35% to about 55% by weight and sea salt ranging from about 0.3 to about 0.9% by weight, wherein the weight ratio of the sum of the saturated compounds in the salmon oil, palm olein and C8/C10 triglyceride to the sum of the mono-unsaturated compounds in the salmon oil, palm olein and C8/C10 triglyceride ranges from about 1.8 to about 2.2, wherein the suni of the dry weight % of all of the components present in the composition is 100%. Another embodiment of the second topical formulation comprises fish oil present in an amount ranging from about 20% to about 30% by weight, palm olein present in about ranging from about 7% to about 9% by weight, C8/C10 triglyceride present in an amount ranging from about 15% to about 18% by weight, C8/C10 fatty acids present in an amount ranging from about 0.5% to about 1.5% by weight, cetyl ester ranging from about 0.3% to about 0.7% by weight; monolaurin, ranging from about 3% to about 5% by weight; said collagen ranging from about 40% to about 50% by weight and sea salt ranging from about 0.4% to about 0.7% by weight, wherein the weight ratio of the sum of the saturated compounds in the salmon oil, palm olein and C8/C10 triglyceride to the sum of the mono-unsaturated compounds in the salmon oil, palm olein and C8/C10 triglyceride ranges from about 1.8 to about 2.2, wherein the sum of the dry weight % of all of the components present in the composition is 100%. In another embodiment, the fish oil is present in an amount ranging from about 22% to about 26% by weight, palm olein is present in about ranging from about 8% to about 9% by weight, C8/C10 triglyceride is present in an amount ranging from about 16% to about 17% by weight, C8/C10 fatty acid is present in an amount ranging from about 0.8% to about 1.2% by weight, cetyl ester is present in an amount ranging from about 0.4% to about 0.6% by weight; monolaurin, is present in an amount ranging from about 3.5% to about 4.5% by weight; fish collagen is present in an amount ranging from about 43% to about 46% by weight and sea saline is present in an amount ranging from about 0.5% to about 0.6% by weight, wherein the weight ratio of the sum of the saturated compounds in the salmon oil, palm olein and triglyceride mixture of C8 and C10 fatty acids to the sum of the mono-unsaturated compounds in the salmon oil, palm olein and triglyceride mixture of C8 and C10 fatty acids ranges from about 1.8 to about 2.2, wherein the sum of the dry weight % of all of the components present in the composition is 100%. In another embodiment, the fish oil is present in an amount ranging from about 24% to about 25% by weight, palm olein is present in about ranging from about 8.2% to about 8.5% by weight, C8/C10 triglyceride present in an amount ranging from about 16.5% to about 16.8% by weight, C8/C10 fatty acid is present in an amount ranging from about 1% to about 1.1% by weight, cetyl ester is present in an amount ranging from about 0.5% to about 0.55% by weight; monolaurin, is present in an amount ranging from about 3.8% to about 4.2% by weight; collagen is present in an amount ranging from about 43.5% to about 44.5% by weight and sea salt is present in an amount ranging from about 0.52% to about 0.62% by weight, wherein the weight ratio of the sum of the saturated compounds in the salmon oil, palm olein and C8/C10 to the sum of the mono-unsaturated compounds in the salmon oil, palm olein and C8/C10 triglyceride ranges from about 1.8 to about 2.2, wherein the sum of the dry weight % of all of the components present in the composition is 100%.

The collagen may be present in an amount ranging from about 35% to 55% by weight. In another embodiment, it is present in about 40% to about 50% by weight, and in another embodiment in about 43% to about 46% by weight.

The salt may be present in an amount ranging from about 0.2% to about 0.9% by weight; in another embodiment, from about 0.3 to about 0.7% by weight; and in another embodiment, about 0.6% by weight.

The actual formulation is interactive with the monolaurin concentration. The monolaurin gels (@>3.5%) to form a structure to make a metastable matrix. Once the gel forms, the ideal amount of collagen is a function of ease of kneading and ease of extrusion.

In an embodiment, the fish oil is salmon oil. In another embodiment, the palm olein is red palm olein. In an embodiment, the collagen is collagen from a marine animal, such as fish collagen. In another embodiment, the composition comprises salmon oil, red palm olein, cetyl esters, MCT containing an average weight ratio of C8/C10 triglyceride of about 60:40 and C8/C10 fatty acid, fish collagen cetyl ester and monlaurin in the amounts described herein. In another embodiment, the second topical formulation comprises salmon oil being present in about 24.9% by weight, palm olein being present in about 8.3% by weight, a mixture of C8 and C10 free fatty acids being present in about 1.0% by weight, C8/C10 fatty acids being present in about 16.6% by weight, cetyl ester being present in about 0.51% by weight; monolaurin being present in about 4.0% by weight; fish collagen being present in about 44.0%, and sea saline being present in about 0.6% by weight.

The collagen formulation is prepared by art-recognized techniques. It is prepared by mixing all of the ingredients except the collagen and sea salt together and heating at 40° C. until thoroughly mixed until the cetyl ester and the monolaurin have melted and then allowing the composition to cool rapidly in an ice bath or cold-wall tank at about room temperature, as described hereinabove with the emollient composition, to firm a first mixture. Once at room temperature, a premix of the collagen and the sea salt, prepared by mixing thoroughly the collagen and the ground sea salt to form a second mixture, is added to the first mixture and thoroughly mixed at about room temperature. Then it is allowed to stand for a time at 5° C. sufficient to harden, such as, for example, at least 8 hours to set the gel and form a collagen matrix. It is believed that the hardening creates a metastable anhydrous mixture into an apparently stable matrix. Without wishing to be bound, it is believed that the microdrops of oil in the collagen are trapped in the cold gel structure such that they cannot flow to the bottom of the container.

The collagen matrix is a metastable matrix because the oil is adsorbed onto the solids. In an embodiment, the weight ratio of sum of C8/C10 triglycerides:sum solids (monolaurin, cetyl ester sea salt @ 25° C.) ranges from about 0.98:1 to 1:02:1, and in another embodiment, the weight ratio is about 1:1.

The sea salt is a surprising process aid in an anhydrous matrix. The sea salt must be ground and then premixed with the collagen. Sea salt acts to make the dry collagen/oil mix into extruded putty. This flow capability is important in treating non-healing wounds. Non-healing wounds have unpredictable crevices and fissures. An anhydrous mixture that can flow into all the wound surfaces is particularly advantageous for wound healing.

Again, this second type composition (collagen composition) does not have a rancid fishy smell.

Both types of compositions (emollient composition, the collagen composition) are all anhydrous.

In both types of topical compositions (emollient composition and the collagen composition), the amount of fish oil is present in significantly greater amounts by weight than cetyl ester. In an embodiment, the weight ratio of fish oil to cetyl ester ranges from about 40:1 to about 60:1, and in another embodiment, from about 44:1 to about 50:1 and in another embodiment from about 46 to about 52 and in another embodiment, about 48.

It is well known that free fatty acid is a skin irritant. Prior art formulations use triglycerides in which the free fatty acid is neutralized and removed. The skin, however, produces free fatty acids and sebum, a wax, as a first line of defense against pathogenic infections. In an embodiment, the weight ratio of C8/C10 fatty acid to cetyl ester is about 2:1. In this weight ratio, the C8/C10 fatty is not irritating. At higher ratios (example 3:1), the composition created a tingling skin sensation, an indicator of future irritation. At a lower ratio (example 1:1), there was no antimicrobial benefit. The weight ratio of about 2:1 retained the silky smooth finish without odor and without skin irritation. Thus the free fatty acid could reinforce the acid mantle of the skin without harm.

In addition, in an embodiment of both types of topical compositions (emollient composition and the collagen composition) the amount of fish oil is present in significantly greater amounts by weight than palm olein. In an embodiment, the weight ratio of fish oil to palm olein ranges from ranges from about 6:1 to about 1.5:1; in another embodiment, it ranges from about 4:1 to about 2:1 and in another embodiment, it is about 3:1. The ranges are selected to maximize the rate at which fish oil is absorbed by intact skin.

Moreover, in both types of topical compositions (emollient composition and the collagen composition), in an embodiment the weight ratio of C8/C10 triglyceride to C8/C10 fatty acid ranges from about 10:1 to about 25:1, and in another embodiment from about 12:1 to about 18:1 and in another embodiment, about 16:1. Free fatty acid is not absorbed by skin. Triglycerides are absorbed. The MCT:FFA ratio was selected to minimize skin irritation and maximize FFA concentration.

Further, in both types of topical compositions (emollient composition and the collagen composition), fish oil is present in greater amounts by weight than C8/C10 triglyceride. In an embodiment, the weight ratio of fish oil to C8/C10 triglyceride ranges from about 1.1:1 to about 3:1; in another embodiment, it ranges from about 1.2:1 to about 2:1 and in another embodiment it ranges from about 1.3:1 to about 1.7:1 in another embodiment, it is about 1.5:1. MCT oil is a penetration enhancing oil. The MCT oil helps transport fish oil into skin before the omega3 fats can oxidize. The ratio was selected to drive fish oil into the skin before it oxidizes.

Moreover, in an embodiment with respect to both types of formulations, (emollient composition and the collagen composition), the amount of C8/C10 triglyceride is present in greater amounts by weight than the palm olein. In an embodiment, the weight ratio of C8/C10 triglyceride to palm olein is about 1.3:1 to about 4:1; in another embodiment, the weight ratio ranges from about 1.5:1 to about 3:1, and in another embodiment, it is about 2:1. The Vitamin E fractions in palm olein do not easily penetrate skin. By mixing the red palm olein with MCT at about a 2:1 ratio, skin staining (by colorful Vitamin E and colorful astaxanthin) is eliminated.

Further in the emollient, composition there is a greater amount of cetyl ester present than monolaurin. In an embodiment, the weight ratio of cetyl ester to monolaurin per gram of fish oil ranges from about 1.1 to about 3:1, in another embodiment, from about 1.4 to about 2:1 and in another embodiment about 1.7:1. On the other hand, in an embodiment in the collagen composition, there is a greater amount of monolaurin present than cetyl ester. In some embodiments of the collagen composition, there is no cetyl ester present. In other embodiments of the collagen composition, the weight ratio of monolaurin to cetyl ester per gram of fish oil ranges from about 3:1 to about 9:1, and in another embodiment, the weight ratio ranges from about 5:1 to about 7:1 and in another embodiment, the weight ratio is about 6:1. Excess monolaurin is added to increase the wax concentration in the collagen matrix for phase stability. Excess monolaurin is added to the collagen matrix (a leave-on product) because monolaurin is a well known, but controversial antimicrobial agent. Monolaurin is the antimicrobial agent in Mother's milk, for example. The controversy is that the activity is not rapid and it does not kill everything and therefore does not meet current FDA definitions of antimicrobial activity. However, in a wound care environment, slow effectiveness is a major benefit. Wounds should not be sterile because microbes create the proteins necessary to autolytically debride the wound. If all bacteria are killed, the wound cannot close. Monolaurin "tilts" the bacterial "playing field" such that commensal bacteria thrive while pathogens are inhibited.

Cetyl ester is also a process aid. The collagen matrix is a metastable mixture in that it is not inherently stable @ 25° C. The doctor wants putty that can be extruded into the wound and flow into all the interstices. The FDA is used to reviewing products that are entirely homogeneous. These competing desires are difficult to execute in practice. In the collagen matrix, the cetyl ester can range up to 1% to thicken the matrix so oil does not "weep" out. The sea salt can be adjusted to maintain the putty consistency. In an embodiment, the material percent changes are very small and the phase stability/viscosity changes are large. Skilled artisans recognize that small changes may be necessary when natural products change during different harvesting seasons. During processing and packaging, the product is kept chilled to prevent weeping so that absolute consistency is maintained. One filled into unit dose packs, the doctor can knead the flexible package to achieve temporary homogeneity and have putty-like flow.

The compositions described herein are topically applied to the skin. "Topical" administration means local, external administration to skin and/or to a wound. The composition may be topically administered directly to all or to part of the area of skin or the wound in need of treatment, or peripherally to the skin area or the wound.

A wide variety of optional components/ingredients may be included in the compositions of the present invention. For example, the compositions may include absorbents, abrasives, anticaking agents, antifoaming agents, antimicrobial agents, binders, biological additives, buffering agents, bulking agents, chemical additives, biocides, denaturants, cosmetic astringents, drug astringents, external analgesics, film formers, humectants, opacifying agents, fragrances, pigments, colorings, essential oils, skin sensates, emollients, skin soothing agents, pH adjusters, plasticizers, preservatives, preservative enhancers, propellants, reducing agents, additional skin-conditioning agents, skin penetration enhancing agents, skin protectants, solvents, suspending agents, emulsifiers, thickening agents, solubilizing agents, sunscreens, sunblocks, ultraviolet light absorbers or scattering agents, sunless tanning agents, antioxidants and/or radical scavengers, chelating agents, sequestrants, anti-acne agents, anti-inflammatory agents, anti-androgens, depilation agents, desquamation agents/exfoliants, organic hydroxy acids, vitamins and derivatives thereof, and natural extracts. Such other materials are known in the art. Nonexclusive examples of such materials are described in Harry's Cosmedcology, 7th Ed., Harry & Wilkinson (Hill Publishers, London 1982); in Pharmaceutical Dosage Forms—Disperse Systems; Lieberman, Rieger & Banker, Vols. 1 (1988) & 2 (1989); Marcel Decker, Inc.; in The Chemistry and Manufacture of Cosmetics, 2nd. ad., deNavarre (Van Nostrand 1962-1965); and in The Handbook of Cosmetic Science and Technology, 1st Ed. Knowlton & Pearce (Elsevier 1993).

The compositions can be formulated as a gel, ointment, cream, balm, or lotion. It may be administered in any one of those forms or administered as an oil-impregnated wipe or spray, such as an aerosol spray, including a bag-on-valve aerosol spray. Topical administration can also be accomplished with a liquid spray, an aerosol, or via iontophoresis, or through the use of liposomes, microbubbles and/or microcapsules. Gels, ointments and creams may be formulated with additives, for example, with an aqueous or oily base with the addition of suitable thickening (e.g., wax, beeswax, PEG 4000, PEG 600, hard paraffin) and/or gelling agents (e.g., hydroxypropyl cellulose). Lotions may be formulated with additives, such as an aqueous or oily base and can also generally contain one or more emulsifying agents (e.g., wool wax alcohol, fatty acid glycol esters), stabilizing agents (e.g., polyoxyethylene sorbitan monolaurate, carboxy methyl cellulose), dispersing agents (e.g., sodium oleate, propylene glycol), suspending agents (e.g., methyl cellulose, chitosan, accacia, carboxymethyl cellulose, tragacanth, pectin), thickening agents, and/or coloring agents (e.g., dyes, lackes). In some embodiments, for example, the topical compositions can include pluronic gels, polaxamer gels, hydrogels containing cellulose derivatives, including hydroxyethyl cellulose, hydroxymethyl cellulose, carboxymethyl cellulose, hydroxypropylmethyl cellulose and mixtures thereof; and hydrogels containing polyacrylic acid (carbopols). Embodiments may also include creams/ointments conventionally used for topical cosmetic or pharmaceutical preparations, e.g., creams based on cetomacrogol emulsifying ointment. The above carriers may include alginate (as a thickener or stimulant), preservatives such as benzyl alcohol, buffers to control pH such as disodium hydrogen phosphate/sodium dihydrogen phosphate, agents to adjust osmolarity such as sodium chloride, and stabilizers such as EDTA. Oil soluble anti-oxidizers, such as Vitamin E, and astaxanthin. Oil soluble vitamins, such as Vitamin D can be added. Oil soluble fragrances such as vanilla, lemon oil and lavender and oil-soluble coloring agents may be added. In addition sebum can be added. Further, benzethonium chloride, methylbenzethonium chloride and benzalkonium chloride may be present.

The stabilized formulation can be applied directly to the skin or wound as a gel, ointment, liquid, cream, or the like as described above. Alternatively, the stabilized formulation is administered in the form of a wound dressing. As used herein, the terms "wound dressing" and "dressing" refer broadly to any substrate when prepared for, and applied to, a wound for protection, absorbance, drainage, improvement of cell environment, etc., and may include any one of the numerous types of substrates and/or backings that are commercially available, including films (e.g., polyurethane films), hydrocolloids (e.g., hydrophilic colloidal particles bound to polyurethane foam), hydrogels (e.g., cross-linked polymers containing about at least 60% water), foams (hydrophilic or hydrophobic), calcium alginates (e.g. nonwoven composites of fibers from calcium alginate), silicone, collagen, keratin, and cellophane (e.g. cellulose with a plasticizer). For example, the stabilized formulation can be applied to the surface of, or incorporated into, a solid contacting layer such as a dressing gauze or matrix. Suitable gauze dressings may include, for example, dry woven or non-woven sponges, swabs, bandages and wraps with varying degrees of absorbency. Exemplary fabric composition may include, for example, cotton, polyester or rayon. In certain embodiments, gauzes and non-woven dressings may be available sterile or non-sterile in bulk and with or without an adhesive border. In certain embodiments the dressings also comprise one or more additional pharmaceutically active compound and/or carrier agent, including for example, saline, oil, zinc salts, petrolatum, xeroform and scarlet red.

Other additives that may be present in the formulation described herein For example, antioxidants and preservatives. Examples of antioxidants include, but are not limited to, tocopherols, ascorbic acid, sodium pyrosulfite, butylhydroxytoluene, butylated hydroxyanisole, edetic acid, and edetate salts, and mixtures thereof. Examples of preservatives include, but are not limited to, citric acid, tartaric acid, lactic acid, malic acid, acetic acid, benzoic acid, and sorbic acid.

In embodiments of the present invention, the composition can comprise any one or more of the additional therapeutically active compounds and pharmaceutically and/or cosmetically acceptable diluents, excipients or carriers described herein. A composition that comprises the stabilized formulation can be formulated for topical application as described herein and sealed in an air tight container suitable for a single use. Such a composition can be used to treat any of the skin conditions and/or wounds described herein, for example a skin condition and/or wound.

The compositions of the present invention are useful for treating wounds and skin conditions. As used herein, a wound is defined as an injury to living tissue of the mammal in which the skin is cut or broken. It includes incisions, cuts, including paper cuts and shaving cuts and burns. However, as defined herein, the wound may or may not be accompanied by bleeding. Examples of wounds treatable by the composition described herein include, but are not limited to, incisions (including surgical incisions), lacerations, abrasions (such as in dermabrasion and microdermabrasions), ulcers, and the like. In some embodiments, the wound is a diabetic wound ulcer.

The wound may be the result of an accidental injury or be the consequence of a medical procedure. The wound may be a surgical incision. The wound may be an ischemic tissue flap, such as in the course of cosmetic surgery. The wound may be one caused in the course of other cosmetic surgery, such as dermabrasion, microdermabrasion, chemical peel, laser resurfacing, etc. The wound may be a chronic injury.

The compositions of the present invention are useful for treating chapped skin and other skin disorders. Examples of skin disorders include acne, psoriasis, eczema, dermatitis, alopecia, rosacea, burns, chapped skin and the like.

The term "acne" is meant to include any skin condition where a skin pore becomes blocked and/or thereby becomes inflamed. The term acne includes without limitation superficial acne, including comedones, inflamed papules, superficial cysts, and pustules; and deep acne, including deep inflamed modules and pus-filled cysts. Specific acne conditions can include, but are not limited to, acne vulgaris, acne comedo, papular acne, premenstrual acne, preadolescent acne, acne venenata, acne cosmetica, pomade acne, acne detergicans, acne excoriee, gram negative acne, acne rosacea, pseudofolliculitis barbae, folliculitis, perioral dermatitis, and hiddradenitis suppurativa. Acne is a common inflammatory pilosebaceous disease characterized by comedones, papules, pustules, inflamed nodules, superficial pus-filled cysts, and (in extreme cases) canalizing and deep, inflamed, sometimes purulent sacs. Acne involves an interaction between hormones, keratinization, sebum, and bacteria that somehow determines the course and severity of acne. It often begins at puberty, when the increase in androgens causes an increase in the size and activity of the pilosebaceous glands. The earliest microscopic change is thought to be intrafollicular hyperkeratosis, which leads to blockage of the pilosebaceous follicle with consequent formation of the comedo, composed of sebum, keratin, and microorganisms, particularly *Propionibacterium acnes*. Lipases from *P. acnes* break down triglycerides in the sebum to form free fatty acids (FFA), which irritate the follicular wall. Retention of sebaceous secretions and dilation of the follicle may lead to cyst formation.

Skin conditions also include, but are not limited to, dermatological conditions linked to disorders of keratinization involving differentiation and proliferation, in particular, acne vulgaris, comedonic or polymorphic acne, nodulocystic acne, acne conglobata, senile acne and secondary acnes such as solar, drug or occupational acne; for other types of keratinization disorders especially ichthyoses, ichthyosiform conditions, Darier's disease, palmoplantar keratoderma, leukoplakia and luecoplakiform conditions or lichen and lichen planus; dermatological disorders having an inflammatory or immunoallergic component, in particular, all forms of psoriases, either cutaneous, mucosal or ungual, and psoriatic rheumatism, and cutaneous atopy such as eczema or respiratory atopy, dry skin, inflammation of the skin, solar erythema, skin allergies or other skin disorders of the epidermis and dermis.

Psoriasis is a skin condition characterized by hyperplasia of keratinocytes resulting in thickening of the epidermis and the presence of red scaly plaques. The lesions in this chronic disease typically are subject to remissions and exacerbations. There are several patterns, of which plaque psoriasis is the most common. Guttate psoriasis, with raindrop shaped lesions scattered on the trunk and limbs, is the most frequent form in children, while pustular psoriasis is usually localized to the palms and soles. The classical inflammatory lesions vary from discrete erythematous papules and plaques covered with silvery scales, to scaly itching patches that bleed when the scales are removed. Psoriasis is a condition in which cell proliferation is increased up to 10 times the normal rate for an individual. The skin is the largest portion of the human body which is comprised of cells within three skin layers. Each of the skin layers is in a constant state of growth with the outer layer being formed of predominantly dead tissue which is naturally being discarded at a normal rate. Replacement of cells from underlying layers is accomplished by cell division and maturation where cells move upwardly and outwardly at a rate which varies dependent upon the age, sex, and/or health of an individual. Psoriasis causes an increased turnover of cells, which in turn increases the rate of cell growth and cell death. This increased rate of cell growth and cell death may result in injuries and/or disorders which accompany the increased synthesis of all tissue components and further elevate the strain placed upon skin or other tissue and the bio-synthetic capabilities of the cells within the affected area.

The terms eczema and dermatitis are generally used names for severe inflammation of the skin, usually with redness, swelling, oozing, rusting or scaling of lesions which are usually itchy. Eczema may take the form of contact dermatitis (due to skin contact with the cause) or atopic dermatitis in individuals who are "atopic" or allergic by nature. If the scalp is involved the disorder is known as seborrheic dermatitis. Dermatitis can be caused by chemicals, plants, shoes, clothing, metal compounds and even medicines used to treat dermatitis. In atopic dermatitis environmental temperature, humidity changes, bacterial skin infections, airborne allergens and garments, e.g., wool, may all bring about dermatitis.

Alopecia is a skin condition that results in the loss of hair on the scalp and elsewhere. It usually starts with one or more small, round, smooth patches and occurs in males and females of all ages. Loss of hair in one or several small spots is common, but it is possible to lose all scalp hair (alopecia totalis), or every hair on the body (alopecia universalis), which is rare.

The skin condition, rosacea is of an unknown origin. It usually affects the middle third of the face causing skin redness, prominent vascularization, papules, pustules and swelling, as well as a predisposition to flushing and blushing. However, rosacea can also occur on other parts of the body including the chest, neck, hack, or scalp. The blood vessels near the skin dilate and become more visible there through, resulting in telangiectasia. The resulting papules and pustules resemble teenage acne, and are frequently mistaken for the same. Unlike acne, rosacea does not have blackheads or whiteheads. Rosacea, however, can occur in all age groups and in both sexes, where it tends to be more frequent in women but more severe in men. The flushing and blushing regions of the face are affected by rosacea. Emotional factors such as anxiety, embarrassment, or stress may evoke or aggravate rosacea. In addition, a flare-up may be caused by environmental or climate variances, and UV exposure is known to aggravate rosacea. Furthermore, diet is also known to aggravate rosacea. Spicy foods, alcoholic beverages, hot beverages, and smoking are known to cause flare-ups. Rosacea is not only an aesthetic complication. Rosacea is a chronic disease that has rarely been documented to reverse its progression. If untreated, the condition worsens and spreads. Untreated rosacea may cause a disfiguring nose condition called rhinophyma, which is characterized by a bulbous, red nose and inflamed cheeks. Severe rhinophyma may require surgery, an invasive procedure that may be avoided by timely treatment. Another problem of advanced rosacea is ocular. Persons afflicted with rosacea may experience conjunctivitis, a burning and grittiness of the eyes. If untreated, it may lead to serious complications such as rosacea keratitis, which damages the cornea and may impair vision.

Burns involve a type of skin integrity rupture. Burns represent one of the most painful processes that can be established in this tissue, needing the establishment of a coordinated therapy to help its recovery and pain treatment. Burns can be caused by several factors, among which, exposure to high or low temperatures, exposure to chemical compounds, by electricity, by exposure to radiation and mechanical friction. Burn severity and its risk are evaluated according to the amount of affected tissue and depth reached. The amount of affected tissue is represented by the percentage of burned corporeal surface (BCS). In this type of evaluation, burns can be divided into small, moderate, large or massive burns, where regions inferior to 15% of BCS, from 15% up to 49% of BCS, from 50% up to 69% of BCS and over 70% of BCS, respectively. The extension of the affected area is determined through Lund-Browder scheme, which takes into consideration the burn proportion, in accordance with the age of the burned patient. Another rule that is most used for determining the extension of the affected area is that known as Wallace Rule or Rule of Nines, a technique less efficient than the foregoing, however, easy to memorize, being very much employed in emergency cases. This rule applies a value equaling nine or nine multiple to the affected parts, being 9% for each superior member, 9% for the head, 18% for each inferior member, 18% for each torso face and 1% for the genitalia.

The classification as first, second and third degree corresponds to burn depth. The first-degree injury corresponds to the burn that affects the skin most external layer (epidermis), not producing hernodynamic alterations, however the affected region is found hyperemic in absence of blisters or phlyctenae. This type of injury can be observed in erythemae resulting from sunrays or heated water. The second-degree injury affects either the epidermis as part of the dermis and is mainly characterized by the formation of blisters or phlyctenae, as those resulting from scalding or thermal injury resulting from overheated liquid. The third-degree injury endangers the totality of skin layers (epidermis and dermis) and, in many cases, can affect other tissues, as the subcutaneous cellular tissue, muscular tissue and bone tissue. Third-degree burns are considered as the most severe of all thermal injuries, producing deforming injuries. For being deeper, it eliminates the nerve endings responsible for shooting the painful message. These types of burns need transplanting for recomposing destroyed tissues, since the structures and organelles necessary for the natural recovery process, were eliminated. Since burns are wounds that involve the skin, they develop afore mentioned complex process of regeneration and recomposition of injured tissue. The speed or grade of re-epithelization of the affected region is small the greater the area involved is, considerably increasing the recovery time, when the injuries start to cover a body surface over 10% or 15%.

Immediately after the burn trauma, an inflammatory process develops wherein various agents are delivered, occurring deposition of fibrins and platelets activated on the wound surface. A matrix rich in organic material is yielded, able to enclosure bacteria and other strange substances, which frequently aggravates the case, due to sepsis that can follow trauma. During this inflammatory process a great quantity of exudates crop out of the burned region, leading the patient to an intense loss of liquids, which, depending on the burn extension and depth, can cause a severe dehydration case. The inflammatory process extends to adjacent tissues, factor that endangers the functions of these tissues initially intact.

Extensive and deep burns cause alterations that are extended far beyond the affected local, such as anatomic, metabolic, physiological, endocrinology and immune alterations, requiring special care. Significant fluid losses, delivery of inflammatory multi-mediators and contamination by bacteria, occur. When disseminated in central organs through circulation, bacteria and inflammatory mediators can cause cardiac endangerment, failure of gastrointestinal mucous integrity and in extreme cases, multi-organic failure.

Hemodynamic alterations that occur after severe thermal injuries include decrease of cardiac output and reduced volume of circulating plasma, contributing all to a hypovolemic shock. Inflammatory mediators (including cytokines, prostaglandin, nitric oxide and superoxide ions) have been implicated in causing further damage to tissues. It is believed that despite local benefit, such mediators induce undesirable effects when reaching significantly high levels. As an example, a greater damage to tissues can be caused by delivery of proteolitic enzymes and superoxide ions of macrophages and activated leucocytes.

Thus, burns are skin conditions that develop unbalance in a series of natural organic mechanisms, not limited to endangered tissues only, but involve numerous organs that can be affected. Additionally, large thermal injuries induce to a sharp increase in basal metabolic rate. Large nitrogen corporeal losses, observed in burned patients, mainly occur due to protein exudation through burned skin and also by the fact that, under such catabolic stress situation, corporeal proteins can become the metabolic substrate used for production of 15 to 20% of total energy required by the organism. Further to these abnormalities, hormonal levels change with an increase in cathecolamines, cortisol and glucagons, in the presence of normal or slightly increased levels of insulin. These hormonal alterations promote increase of proteolysis and lipolysis. Thus, the entire complex process is characterized by imbalance. The quick recovery of the skin of a burned mammal is of utmost importance for recovery of his normal organic functions.

Other skin conditions can include dry/chapped skin. In addition, vaginal dryness and erectile dysfunction are also treatable by the present compositions. Without wishing to be bound, these are partially a function of circulation impairment. When the composition is absorbed in these site-sensitive areas, circulation increases by reducing inflammation in the lymph and venous systems. Blood flow increases.

In another embodiment, the compositions are directed to treating Peripheral artery disease (PAD), which is a narrowing of the peripheal arteries to the legs, stomach, arms, and head. After vascular surgery of a subject having peripheral arterial disease (PAD), a topical composition of any of the compositions described herein, can be applied to the area where the surgery took place. For example, if PAD is in the legs, after vascular surgery in the legs, the composition described herein are topically applied to the legs lower leg skin to increase blood circulation at the skin surface. For example, the composition may be applied as a spray.

Thus, the methods disclosed herein are useful for treating or ameliorating the skin against the effects of environmental conditions. According to an aspect of the present invention, either one or both types of compositions, i.e., emollient or collagen composition described hereinabove is (are) applied topically to at least the part of the body of the patient containing the chapped skin or other skin condition or wound.

Various treatments may be employed. Skin surfaces of the most concern tend to be those not typically covered by clothing such as facial skin surfaces, hand and arm skin surfaces, foot and leg skin surfaces, and neck and chest skin surfaces. In particular, facial skin surfaces, including the forehead, perioral, chin, periorbital, nose, and/or cheek skin surfaces, may be treated with the compositions described herein.

The treatment method may include applying the composition(s) to a previously identified area of skin in need of treatment, or an area where one seeks to prevent, treat or reduce the appearance of chapped skin or other skin disorders. Many regimens exist for the application of the composition(s). The composition(s) may be applied at least once a day, twice a day, or on a more frequent daily basis, during a treatment period. When applied twice daily, the first and second applications are separated by at least 1 to 12 hours.

Typically, the composition(s) may be applied in the morning and/or in the evening before bed.

The treatment period is ideally of sufficient time to provide an improvement in the appearance of the skin. The treatment period may be at least 1 week, and in some embodiments the treatment period may last about 4 weeks, 8 weeks, or 12 weeks. In certain embodiments, the treatment period will extend over multiple months (i.e., 3-12 months) or multiple years. In one embodiment the composition is applied at least once a day during a treatment period of at least 4 weeks, 8 weeks, or 12 weeks. In one embodiment the composition is applied twice a day during a treatment period of at least 4 weeks, 8 weeks, or 12 weeks.

Effective amounts of each of the compositions are applied topically to the area to be treated. The dose varies with the individual and the skin condition. The ideal dose is that dose that provides as much of the compositions as the skin will absorb. An excess amount of the compositions on the surface of the skin can turn rancid. Patients who used the compositions described herein found that applying the compositions to the areas to be treated just prior to showering was the most effective way to administer these compositions. The skin absorbs all it can; the shower washes off the excess. A silky smooth, odorless finish remains on the skin for 24 hours. The dosage regimen for treating skin conditions and/or wounds is selected in accordance with a variety of factors, including the age, weight, sex, and medical condition of the patient, the severity of the condition, the route of administration, pharmacological considerations such as the activity, efficacy, pharmacokinetic and toxicology profiles of the particular composition used, whether a dressing or drug delivery system is used and whether the composition is administered as part of a drug combination.

The doses may be administered in single or divided applications. The doses may be administered once, or application may be repeated. Application may be repeated weekly until skin and/or wound healing is promoted, or a repeat application may be made in the event that healing slows or is stalled. Doses may be applied 1-7 days apart, or more. In the case of a chronic skin condition or wound, repeat applications may be made, for example, one or more times per day, weekly, or bi-weekly, or monthly or in any other frequency for example if and when healing slows or is stalled. For some indications more frequent dosing such as hourly application may be employed.

In an embodiment, all both types of compositions are applied to the wound or skin condition in the treatment regimen. The first composition applied is the first type of composition described hereinabove, the emollient oil and it is applied topically to the area on the skin to be treated. The second composition applied is the collagen composition, and is applied to cover the wound or skin disorder, if the wound has depth, it is applied to fill the wound depth. The skin condition or wound may then be covered by gauze or band-aid or any other covering or dressing that is typically used to protect the skin-condition or wound from infection. In another embodiment, especially when there is no bleeding or if the wound is a minor cut, such as a paper cut, after the collagen layer is applied, the wound or skin condition is not covered.

Without wishing to be bound, it is believed that the short chain length and polyunsaturated oils in the C8/C10 triglyceride are rapidly absorbed into the skin. The long chain, omega-3 polyunsaturated fats (PUFA) are enzymatically modified by the body to make compounds useful in normal body functions. The PUFA are also naturally anti-inflammatory compounds. As such they reduce resistance in the intradermal capillaries that drain the dermis. Swelling is reduced and surface circulation increases. [There is a visible blush color on treated skin and an associated temperature rise as blood flow increases.] The C8/10 fats also are rapidly absorbed and are useful in normal metabolism.

Without wishing to be bound, it is believed that the monolaurin is a process aid for helping PUFA be rapidly absorbed into the dermis and thus not get oxidized on the skin surface.

Further, without wishing to be bound, Cetyl ester is a wax that does not get absorbed and is not subject to oxidation. It covers slowly absorbed unsaturated fats (like C18:1) to help prevent their oxidation. There is some C18:0 fat in the salmon oil. It becomes part of the waxy cover layer.

Collagen Matrix

Without wishing to be bound, it is believed that the collagen matrix incorporates the oil with fish collagen that allows collagen administration without adding moisture to the wound. The butter-like texture allows the collagen to flow into the interstices of complex wound cavities.

It is believed that the sea salt has a special role in that it makes wound exudate electrically conductive. Periwound charge is negative; wound bed electrical charge is positive. Opposite charges attract which tends to pull the periwound over the wound bed and close the wound.

It is also believed that the periwound/wound bed interface is fragile because periwound skin is attacked by the enzymes in wound exudate, a root cause of wound expansion. Without wishing to be bound, it is further believed that the fish collagen absorbs wound exudate; the C8/C10 fatty acid lowers the pH to inhibit enzymes such as MMP (matrix metalloprotein). The net effect is to adjust the wound exudate to be more conducive to healing.

Without wishing to be bound, it is believed that C8/C10 triglyceride helps control moisture loss. It is also believed that the monolaurin helps control the bacterial burden in the wound bed. The wound should not be sterile, the bioburden should be balanced. Bacteria create the enzymes that help the healing process.

The collagen matrix is best added as a unit dose, so the practitioner can quantify wound volume over time. It can however be added from a jar, multi-use tube or other bulk dispenser.

Each product can be used independent of the other, but there is a synergy when used together.

The C8/C10 triglyceride increases circulation in the skin independently of all else. This benefit is particularly important after the wound has healed as blood flow into and out of the lower extremity helps prevent future skin breakdowns.

The collagen matrix is a rich source of collagen in the wound that helps rebuild skin structure in well-known ways. Applying it as a butter-like anhydrous product increases the mass of collagen that can be filled into the wound volume.

The synergy comes when both products are used as a system. The collagen helps provide structure in the wound bed. The sum of all the oils increases blood flow to the lower extremities, the periwound and the wound bed. The C8/C10 fatty acids and monolaurin help control pathogen populations while still retaining the bacterial activity needed to produce beneficial autolytic enzymes The sea salt allows opposite charged surface skin to migrate towards the wound bed and accelerate wound closing.

Packaging also can affect the odor of fish oil mixtures. A package has to be oxygen free inside the container and not allow oxygen to migrate through the container.

An aerosol can is a particularly valuable container because the propellant atomizes the oil into very small droplets that can be spread over the skin without pooling of oil. This helps accelerate absorption into the skin to further limit the omega3 fats' exposure to oxygen.

The following non-limiting examples further illustrate the invention.

Example 1

An anhydrous oily ingredient was prepared as follows:

| Component | Wt ratio | weight % |
|---|---|---|
| Salmon oil | 3 | 47.85% |
| Red palm olein | 1 | 15.95% |
| Medium-chain triglyceride(s) of a mixture of C8 and C10 fatty acids | 2 | 31.90% |
| Mixture of C8/C10 fatty acids | | 4.00% |
| Monolaurin | | 0.30% |

The above components were mixed together at 40° C. until thoroughly mixed and allowed to cool. The resulting product was s homogenous oil. The resulting product did not exhibit the expected rancid fishy oil odor. The characteristic free fatty acids odor remained, but it was not a lingering odor.

From several experiments not shown, it was determined that 0.3% monolaurin by weight was necessary with respect to this embodiment to substantially eliminate the fishy oil and still have a single phase oil.

Example 2

The following was prepared as an emollient spray:

| Component | weight % |
|---|---|
| Salmon oil | 48.2% |
| Red palm super olein | 16.07% |
| Medium-chain triglyceride(s) of a mixture of C8 and C10 fatty acids | 32.1% |
| Mixture of C8/C10 fatty acids | 2.0% |
| Cetyl esters | 1.0% |
| Monolaurin | 0.6% |

This was prepared using the procedure of Example 1.

This product did not exhibit the rancid fishy smell associated with fish oil.

Example 3

The following formulation comprised of collagen was prepared from the following components:

| Component | Wt ratio | weight % |
|---|---|---|
| Salmon oil | 3 | 24.96 |
| Red palm olein | 1 | 8.32 |
| Medium-chain triglycerides of a mixture of C8 and C10 fatty acids | 2 | 16.64 |
| Mixture of C8/C10 fatty acids | | 2.08 |
| Monolaurin | | 4.00 |
| Fish collagen | | 44.00 |

Except for the collagen, all of the components listed above were mixed together and heated together at 40° C. until thoroughly mixed. The mixture was allowed to cool to 34.3° C. until a gel formed. At this temperature, the collagen was added to the mixture and mixed together. An anhydrous paste formed, and it does not have the rancid fishy smell.

The anhydrous collagen blend was paste. The paste first formed at about 2.5% monolaurin. The paste was slushy at about 3% monolaurin. At about 3.5% monolaurin the gel became firm enough that an open container containing same could be inverted without gel flowing. At 4%, the admixture had the texture of "jam" mixed with "sand" (the dry collagen). The oils were tied up in the gel and do not bleed out of the admixture.

Surprisingly, increasing fish collagen above 44% thickened the blend, but did not make the mixture phase stable, even though the mixture was too thick to extrude. The problem was resolved by increasing the monolaurin to 4% and allowing the oil/monolaurin 40° C. to cool to <34.3° C. to form a first gel and then admixing in the anhydrous fish collagen. This mixture was phase stable and could be extruded as a soft "toothpaste". In this instance, the monolaurin concentration was 3.5% (i.e. separated after 2 weeks when oil and collagen are mixed at T>34.3° C.; it did not separate when oil and collagen are mixed at T<34.3° C.). In other words, stabilizing the oil as a gel first and then admixing dry collagen into the gel made the mixture phase stable at T<gel melting point and still be extruded.

The ratios of oils did not appear to be critical in the phase stability of the oil/collagen admixture.

This product did not have the rancid fishy smell associated with fish oil.

Example 4

The following components were mixed together thoroughly.

| Component | moles | Weight % |
|---|---|---|
| Benzethonium chloride | 0.00045 | 0.200 |
| Mixture of C8/C10 fatty acids | 0.00045 | 0.070 |
| Sea Salt (5 lb. bag) | | 0.900 |
| Water (QS) | | 98.83 |

In this composition, Sea Salt, benzethonium chloride and the mixture of C8/C10 fatty acids C8/10 provided an unique buffer. The benzethonium chloride and mixture of fatty acids react to form soap and release a proton, lowering pH. The soap further reacts to form a tertiary amide acid hydrate, consuming 1 of 3 protons released during soap making. The pH rose slightly.

It is noted that the acid hydrate formed a film over the treated skin. The film retained the antimicrobial activity of benzethonium chloride. The film was not antimicrobial, but was rather an antimicrobial barrier.

Comparative Example 1

The products of Example 3 and Example 4 were mixed together in a 1:1 weight ratio. However, several negative attributes were discovered.

The residual skin feel after rubbing in oil was acceptable, but not silky smooth. If salt were added to an anhydrous collagen mixture, the gel freezing point became depressed. When the isotonic product was packed into a wound, the product melted too fast.

Example 5

The following composition was prepared as follows:

| Component | wt ratio | weight % |
|---|---|---|
| Salmon oil | 3 | 24.50 |
| Red palm olein | 1 | 8.17 |
| Medium-chain triglycerides of a mixture of C8 and C10 fatty acids | 2 | 16.33 |
| Mixture of C8/C10 fatty acids | | 2.1 |
| Monolaurin | | 4.0 |
| Fish collagen | | 44.0 |
| Sea salt | | 0.90 |

The above components except for the collagen and the sea salt were mixed together at 40° C. After these components were thoroughly mixed, the mixture was allowed to cool to 30° C. A gel formed. Then a premix of the collagen and the sea salt were added to the gel and mixed thoroughly therewith. The mixture was dried. The final composition did not have the rancid fishy smell of fish oil.

The resulting product was a solution to the problem posed in Comparative Example 1.

Cetyl ester was introduced in this example. By adding Cetyl Esters NF to the anhydrous oil created a silky smooth skin surface (finish). Further, the sea salt was added. If the salt is added after the gel is fully formed, the freezing point depression does not occur.

If a wound hydrogel sheet is used to immediately cover the collagen paste, then the released oil stays in the wound until absorbed. This embodiment releases oil to the periwound area as it retains the collagen in the wound.

Example 6

The following components were mixed together to form a collagen gel in accordance with the procedure of Example 5.

| Component | Weight % |
|---|---|
| Salmon oil | 24.92 |
| Red palm olein | 8.31 |
| Medium-chain triglycerides of a mixture of C8 and C10 fatty acids | 16.62 |
| Mixture of C8/C10 fatty acids | 1.03 |
| Cetyl ester | 0.51% |
| Monolaurin | 4.00 |
| Fish collagen | 44.00 |
| Sea salt | 0.6% |

The resulting product did not have the rancid fishy smell. The product is readily extruded (soft butter). Some oil bleeds out of this mixture after 48 hours. It was found that if the as-made mixture is hardened @ 5° C. for 24 hours, then the oil does not bleed out even after reverting to room temperature.

More surprisingly, the monolaurin level dissolves in the oil blend at low concentrations, but forms gels at higher concentration. If the monolaurin, marine oil, vegetable oil, C8/C10 fatty acid blend is allowed to cool below the gel formation temperature (34.3° C.) to form a hard gel and then admixed with dry fish collagen, the anhydrous oil/collagen mixture is stable at ambient temperature and can be easily extruded Example 7

The collagen composition of Example 6 is applied to 3 separate patients, one having a venous ulcer, a second one having a diabetic foot ulcer or a third one having a pressure ulcer. The admixture is extruded onto the wound bed. The composition is rubbed on the periwound and rubbed in from the tip of the toe to the knee. In a few days, all three users observe that the dry skin flakes off; pink, small pore skin replaces damaged and dying skin. In addition, leg swelling is reduced and the pain is reduced. The result is pink, small pore, healthy skin. As the patient sees his/her skin texture, color and smoothness improve, compliance with the protocol improves.

Without wishing to be bound, the following believed to have occurred:

1. The collagen absorbs exudate and rejects the admixed oil.
2. The skin absorbs the oil
3. Fish collagen has a $T_g$ (glass transition temperature) <body temperature.
   a. The body-heated fish collagen flows into all the nooks and crannies of the wound.
4. Monolaurin is described in the literature as an antimicrobial compound.
   a. In this example, monolaurin is not an antimicrobial compound but rather helps reduce bacterial growth in the collagen dressing.
5. Fish collagen, like any other collagen, provides a matrix for skin growth.
6. The C8/C10 fatty acid helps the wound bed maintain a slightly acidic pH.
   a. The literature teaches that slightly acid pH helps wound healing.

Without wishing to be bound, it is believed that the mechanism of action is:

1. The oils (fish oil, C8/C10 triglyceride and palm olein) are rapidly absorbed into the skin.
2. Dying skin exfoliates with the solvent action of the oil blend.
3. The C8/C10 fatty acid mixture, cetyl ester and monolaurin are not absorbed, but form a film on the skin surface.
4. The C8/C10 fatty acid mixture and monolaurin reinforce the acid mantle of the skin, the indigenous first line of defense to bacterial infection.
5. Meanwhile the polyunsaturated, omega3, very long chain fatty acids (PUFA) are naturally anti-inflammatory compounds.
6. The heart pumps blood into the legs; the venous system allows the blood to drain back to the heart; waste products leave via the lymph system.
7. The PUFA reduce inflammation in the venous and lymph systems, draining fluid from the legs.
8. With better drainage, there is less painful swelling.
9. The fatty acids and naturally occurring antioxidant compounds (astaxanthin in salmon oil and full spectrum Vitamin E in the red palm olein) help new, healthy skin to grow and gradually replace old, damaged skin.
   a. The result is pink, small pore, healthy skin.

Example 8

Patient CY is a diabetic with neuropathy in both feet. Nothing relieved the pain and he had to retire from his job prematurely. CY used the emollient composition described herein in example 2 for 6 weeks. The pain was gone. The swelling stopped. His skin health went from dry flaking skin to pink, small pore normal skin. He stopped using the composition when his spray can was empty. Pain returned and his skin became dry and flaked again. CY was supplied with fresh composition and his pain went away and the skin became pink. Continuous treatment with the composition significantly improved his quality of life.

Example 9

Patient AM, a medical doctor, uses the spray comprised of the composition of Example 2 for vaginal dryness. She reports that intimate flesh has apparent increased circulation and sensitivity.

Example 10

Diabetic patient NA is due for podiatric surgery. He used the oil for one week as a pre-op treatment. His attending physician reports that NA healed faster than expected.

Example 11

The example 6 formulation is remade but cetyl ester is increased to 0.75% and C8/C10 fatty acid is reduced to 0.801%. No other changes are made. The product retains a putty like consistency and oil does not bleed out of the matrix.

Example 12

The composition of Example 2 is used as an adjunct to vascular surgery to mitigate peripheral arterial disease (PAD). The surgery opens up arterial blockages in major and minor vessels, typically in the lower leg, but does not address the micro capillaries that distribute blood to individual cells. The Example 2 composition is sprayed onto the leg daily for 30 days to reduce inflammation in the micro capillaries. The overall healing rate of the surgery is improved 12%.

The above preferred embodiments and examples were given to illustrate the scope and spirit of the present invention. These embodiments and examples will make apparent to those skilled in the art other embodiments and examples. The other embodiments and examples are within the contemplation of the present invention. Therefore, the present invention should be limited only by the amended claims

What is claimed is:

1. An anhydrous topical composition comprising fish oil in an amount ranging from about 30 to about 70% by weight, palm olein present in an amount ranging from about 10% to about 20% by weight, C8/C10 fatty acid in an amount ranging from about 0.5% to about 4% by weight, C8/C10 triglycerides present in an amount ranging from about 25% to 35% by weight, cetyl ester ranging from about 0.5% to about 2% by weight and monolaurin ranging from about 0.5% to about 2% by weight, wherein the weight ratio of the sum of the saturated compounds in the fish oil, palm olein and C8/10 triglycerides to the sum of the mono-unsaturated compounds in the fish oil, palm olein and C8/C10 fatty acids ranges from about 1.8 to about 2.2, wherein the sum of the dry weight percent of all of the components present is equal to 100%.

2. The anhydrous topical composition according to claim 1 wherein the fish oil is salmon oil.

3. The anhydrous topical composition according to claim 1 wherein the palm olein is red palm olein or red palm super olein.

4. The anhydrous topical composition according to claim 1 wherein the composition is a spray, an oil-impregnated wipe, a liquid or a gel.

5. The anhydrous topical composition according to claim 1 which comprises about 48% salmon oil by weight, about 16% red palm super olein by weight, about 1.0% cetyl ester by weight, about 0.6% monolaurin by weight, C8/C10 fatty acid in about 2% by weight, and a C8/C10 triglyceride in about 32% by weight.

6. An anhydrous topical composition comprising fish oil present in an amount ranging from about 20% to about 40% by weight, palm olein present in an amount ranging from about 6% to about 10% by weight, C8/C10 triglyceride present in an amount ranging from about 14% to 18% by weight, cetyl ester ranging from about 0.3% to about 1% by weight; monolaurin ranging in an amount from about 3% % to about 6% by weight; collagen having a glass transition temperature less than 37° C. ranging in an amount from about 35% to about 55% by weight and sea salt ranging in an amount from about 0.3 to about 0.9% by weight, wherein the weight ratio of the sum of the saturated compounds in the fish oil, palm olein and C8/C10 triglyceride to the sum of the mono-unsaturated compounds in the fish oil, palm olein and C8/C10 triglyceride ranges from about 1.8 to about 2.2, wherein the sum of the dry weight percent of all of the components present is equal to 100%.

7. The anhydrous topical composition according to claim 6 wherein the fish oil is salmon oil.

8. The anhydrous topical composition according to claim 6 wherein the collagen is fish collagen.

9. The anhydrous topical composition according to claim 6 wherein the palm olein is red palm olein.

10. The anhydrous topical composition according to claim 6 in the form of a gel, a paste or a gel impregnated wipe.

11. The anhydrous topical composition according to claim 6 comprising salmon oil being present in about 24.9% by weight, palm olein being present in about 8.3% by weight, C8/C10 fatty acids being present in about 1.0% by weight, C8/C10 triglyceride being present in about 16.6% by weight, cetyl ester being present in about 0.51% by weight; monolaurin being present in about 4.0% by weight; fish collagen being present in about 44.0%, and sea saline being present in about 0.6% by weight.

12. A method of treating a wound or skin condition on a subject which comprises applying on the wound or skin condition an effective amount of an anhydrous topical composition according to claim 1.

13. A method of treating a wound or skin condition on a subject which comprises applying on the wound or skin condition an effective amount of an anhydrous topical composition according to claim 6.

14. The composition according to claim 1 wherein the weight ratio of the sum of the saturated compounds in the fish oil, palm olein and C8/C10 triglyceride to the sum of the mono-unsaturated compounds in the fish oil, palm olein and C8/C10 triglyceride ranges from about 1.9 to about 2.1.

15. The composition according to claim 1 wherein the weight ratio of the sum of the saturated compounds in the fish oil, palm olein and C8/C10 triglyceride to the sum of the mono-unsaturated compounds in the fish oil, palm olein and C8/C10 triglyceride ranges from about 1.95 to about 2.05.

16. The composition according to claim 1 wherein the weight ratio of the sum of the saturated compounds in the fish oil, palm olein and C8/C10 triglyceride to the sum of the mono-unsaturated compounds in the fish oil, palm olein and C8/C10 triglyceride is about 2.

17. The composition according to claim 1 which comprises fish oil, containing omega-3 fatty acid present in an amount ranging from about 45% to about 52% by weight, palm olein present in an amount ranging from about 14% to about 18% by weight, a mixture of free fatty acids of C8 to C10 in a weight ratio of C8 to C10 fatty acid of 1.3 to 1.6, said mixture present in an amount ranging from 1% to about 3% by weight, medium-chain triglyceride(s) of a mixture of C8 and C10 fatty acids present in an amount ranging from about 28% to 34% by weight, cetyl ester ranging from about 1.0% to about 2% by weight and monolaurin, ranging from about 0.5% to about 1.5% by weight, wherein the weight ratio of the sum of the saturated compounds in the fish oil, palm olein and triglyceride mixture of C8 and C10 fatty acids to the sum of the mono-unsaturated compounds in the fish oil, palm olein and triglyceride mixture of C8 and C10 fatty acids ranges from about 1.8 to about 2.2, wherein the sum of the dry weight % of all of the components present in the composition is 100%.

18. The composition according to claim 1 wherein the weight ratio of fish oil to cetyl ester ranges from about 40:1 to about 60:1.

19. The composition according to claim 1 wherein the weight ratio of C8/C10 fatty acid to cetyl ester is about 2:1.

20. The composition according to claim 1 wherein the weight ratio of fish oil to palm olein ranges from ranges from about 6:1 to about 1.5:1.

21. The composition according to claim 8 wherein the weight ratio of C8/C10 triglyceride to C8/C10 fatty acids ranges from about 10:1 to about 25:1.

22. The composition according to claim 1 wherein the weight ratio of C8/C10 triglyceride to palm olein ranges from about 1.3:1 to about 4:1.

23. The composition according to claim 1 wherein the weight ratio of cetyl ester to monolaurin per gram of fish oil ranges from about 1.1 to about 3:1.

24. The composition according to claim 6 wherein the weight ratio of the sum of the saturated compounds in the fish oil, palm olein and C8/C10 triglyceride to the sum of the mono-unsaturated compounds in the fish oil, palm olein and C8/C10 triglyceride ranges from about 1.9 to about 2.1.

25. The composition according to claim 6 wherein the weight ratio of the sum of the saturated compounds in the fish oil, palm olein and C8/C10 triglyceride of C8 to the sum of the mono-unsaturated compounds in the fish oil, palm olein and C8/C10 triglyceride ranges from about 1.95 to about 2.05.

26. The composition according to claim 6 wherein the weight ratio of the sum of the saturated compounds in the fish oil, palm olein and triglyceride mixture of C8 and C10 fatty acids to the sum of the mono-unsaturated compounds in the fish oil, palm olein and triglyceride mixture of C8 and C10 fatty acids is about 2.

27. The composition according to claim 6 which comprises fish oil present in an amount ranging from about 20% to about 30% by weight, palm olein present in about ranging from about 7% to about 9% by weight, a medium-chain triglyceride(s) of a mixture of C8 and C10 fatty acids present in an amount ranging from about 15% to about 18% by weight, a mixture of C8 and C10 free fatty acids present in an amount ranging from about 0.5% to about 1.5% by weight, cetyl ester ranging from about 0.3% to about 0.7% by weight; monolaurin, ranging from about 3% to about 5% by weight; said collagen ranging from about 40% to about 50% by weight and sea salt ranging from about 0.4 to about 0.7 by weight, wherein the weight ratio of the sum of the saturated compounds in the fish oil, palm olein and triglyceride mixture of C8 and C10 fatty acids to the sum of the mono-unsaturated compounds in the fish oil, palm olein and triglyceride mixture of C8 and C10 fatty acids ranges from about 1.8 to about 2.2, wherein the sum of the dry weight % of all of the components present in the composition is 100%.

28. The composition according to claim 6 which comprises fish oil present in an amount ranging from about 22% to about 26% by weight, palm olein present in about ranging from about 8% to about 9% by weight, a medium-chain triglyceride(s) of a mixture of C8 and C10 fatty acids present in an amount ranging from about 16% to about 17% by weight, a mixture of C8 and C10 free fatty acids present in an amount ranging from about 0.8% to about 1.2% by weight, cetyl ester present in an amount ranging from about 0.4% to about 0.6% by weight; monolaurin, present in an amount ranging from about 3.5% to about 4.5% by weight; fish collagen present in an amount ranging from about 43% to about 46% by weight and sea saline is present in an amount ranging from about 0.5% to about 0.6% by weight, wherein the weight ratio of the sum of the saturated compounds in the fish oil, palm olein and triglyceride mixture of C8 and C10 fatty acids to the sum of the mono-unsaturated compounds in the fish oil, palm olein and triglyceride mixture of C8 and C10 fatty acids ranges from about 1.8 to about 2.2, wherein the sum of the dry weight % of all of the components present in the composition is 100%.

29. The composition according to claim 6 wherein the fish oil is present in an amount ranging from about 24% to about 25% by weight, palm olein is present in about ranging from about 8.2% to about 8.5% by weight, a medium-chain triglyceride(s) of a mixture of C8 and C10 fatty acids is present in an amount ranging from about 16.5% to about 16.8% by weight, a mixture of C8 and C10 free fatty acids is present in an amount ranging from about 1% to about 1.1% by weight, cetyl ester is present in an amount ranging from about 0.5% to about 0.55% by weight; monolaurin, is present in an amount ranging from about 3.8% to about 4.2% by weight; collagen is present in an amount ranging from about 43.5% to about 44.5% by weight and sea salt is present in an amount ranging from about 0.52% to about 0.62% by weight, wherein the weight ratio of the sum of the saturated compounds in the fish oil, palm olein and triglyceride mixture of C8 and C10 fatty acids to the sum of the mono-unsaturated compounds in the fish oil, palm olein and triglyceride mixture of C8 and C10 fatty acids ranges from about 1.8 to about 2.2, wherein the sum of the dry weight % of all of the components present in the composition is 100%.

30. The composition according to claim 6 wherein the weight ratio of fish oil to cetyl ester ranges from about 40:1 to about 60:1.

31. The composition according to claim 6 wherein the weight ratio of C8/C10 fatty acid to cetyl ester is about 2:1.

32. The composition according to claim 6 wherein the weight ratio of fish oil to palm olein ranges from ranges from about 6:1 to about 1.5:1.

33. The composition according to claim 6 wherein the weight ratio C8/C10 triglyceride to C8/C10 fatty acids ranges from about 10:1 to about 25:1.

34. The composition according to claim 6 wherein the weight ratio of C8/C10 triglyceride to palm olein ranges from about 1.3:1 to about 4:1.

35. The composition according to claim 6 wherein the weight ratio of monolaurin to cetyl ester per gram of fish oil ranges from about 3:1 to about 9:1.

36. The method according to claim 12 wherein the fish oil is salmon oil.

37. The method according to claim 13 wherein the fish oil is salmon oil.

38. A method of treating the lower leg skin after vascular surgery for peripheral arterial disease comprising topically applying to the lower leg skin an effective amount of a composition according to claim 1.

39. A method of treating the lower leg skin after vascular surgery for peripheral arterial disease comprising topically applying to the lower leg skin an effective amount of a composition according to claim 6.

40. An anhydrous topical composition comprised of fish oil in an amount ranging from about 30% by weight to about 70% by weight, monolaurin present in an amount ranging from about 0.5% to about 2% by weight, cetyl ester present in an amount ranging from about 0.5% to about 2% by weight.

41. The anhydrous topical composition of claim 40, wherein the weight ratio of cetyl ester to monolaurin ranges from about 5:1 to about 1:1.

42. The anhydrous topical composition according to claim 40 wherein the cetyl ester is present in a greater amount by weight than monolaurin.

43. A method of treating a wound or skin condition on a subject which comprises applying on the wound or skin condition an effective amount of an anhydrous topical composition according to claim 40.

44. The method according to claim 38 wherein the fish oil is salmon oil.

45. The method according to claim 39 wherein the fish oil is salmon oil.

46. A method for removing the rancid fish smell from a topical fish oil composition in comprising fish oil in an amount ranging from about 30% to about 70% by weight, palm olein present in an amount ranging from about 10% to about 20% by weight, C8/C10 fatty acid in an amount ranging from about 0.5% to about 4% by weight, C8/C10 triglyceride present in an amount ranging from about 25% to 35% by weight, and cetyl ester ranging from about 0.5% to about 2% by weight, wherein the weight ratio of the sum of the saturated compounds in the fish oil, palm olein and C8/C10 triglycerides to the sum of the mono-unsaturated compounds in the fish oil, palm olein and C8/C10 fatty acid ranges from about 1.8 to about 2.2, wherein the sum of the dry weight percent of all of the components present is equal to 100%, and wherein collagen is not present therein, said method comprising adding to and mixing with the fish oil composition monolaurin to a concentration ranging from about 0.5% to about 2% by weight.

47. The method according to claim 46 wherein the fish oil is present in an amount ranging from about 40% to about 60% by weight.

48. The method according to claim 46 wherein cetyl ester is additionally added and mixed with the monolaurin and the fish oil composition.

49. The method according to claim 48 wherein the weight ratio of cetyl ester to monolaurin per gram of fish oil ranges from about 2:1 to about 0.12:1.

50. The method according to claim 46 wherein the fish oil is salmon oil.

* * * * *